(12) United States Patent
Quinones et al.

(10) Patent No.: US 7,192,978 B2
(45) Date of Patent: Mar. 20, 2007

(54) PYRROLIDINIUM DERIVATIVES

(75) Inventors: Maria Prat Quinones, Barcelona (ES); Maria Dolors Fernandez Forner, Barcelona (ES)

(73) Assignee: Almirall Prodesfarma AG, Baar/ZG (CH)

( * ) Notice: Subject to any disclaimer, the term of this patent is extended or adjusted under 35 U.S.C. 154(b) by 0 days.

(21) Appl. No.: 10/510,680

(22) PCT Filed: Apr. 11, 2003

(86) PCT No.: PCT/EP03/03786

§ 371 (c)(1),
(2), (4) Date: Jul. 20, 2005

(87) PCT Pub. No.: WO2003/087094

PCT Pub. Date: Oct. 23, 2005

(65) Prior Publication Data

US 2005/0282875 A1   Dec. 22, 2005

(30) Foreign Application Priority Data

Apr. 16, 2002 (ES) ............................... 200200889

(51) Int. Cl.
A61K 31/40 (2006.01)
A61K 31/381 (2006.01)
A61K 31/341 (2006.01)
C07D 207/00 (2006.01)
C07D 409/08 (2006.01)
C07D 307/40 (2006.01)
C07D 405/02 (2006.01)

(52) U.S. Cl. ............... 514/422; 514/424; 514/444; 548/518; 548/527; 549/60; 549/83; 549/479

(58) Field of Classification Search ............... 514/422, 514/424; 548/527, 517
See application file for complete search history.

(56) References Cited

U.S. PATENT DOCUMENTS

| | | | |
|---|---|---|---|
| 2,956,062 A | 10/1960 | Lunsford | |
| 3,301,869 A | 1/1967 | Lunsford | |
| 3,714,357 A | 1/1973 | Gueremy et al. | |
| 6,307,060 B1 | 10/2001 | Noe et al. | |
| 6,846,835 B2 | 1/2005 | Ogino et al. | |
| 2002/0173536 A1 | 11/2002 | Noe et al. | |
| 2003/0191316 A1 | 10/2003 | Ogino et al. | |
| 2003/0220400 A1 | 11/2003 | Noe et al. | |
| 2005/0065211 A1 | 3/2005 | Ogino et al. | |

FOREIGN PATENT DOCUMENTS

| | | |
|---|---|---|
| EP | 0 863 141 | 9/1998 |
| EP | 1 302 458 | 4/2003 |
| FR | 2 155 927 | 5/1973 |
| WO | WO 98/21183 | 5/1998 |
| WO | WO 01/04118 | 1/2001 |
| WO | WO 02/04402 | 1/2002 |
| WO | WO2002-IB5590 | * 12/2002 |

OTHER PUBLICATIONS

Franko, Bernard V. et al., "Derivatives of 3-Pyrrolidinols-III. The Chemistry, Pharmacology and Toxicology of some N-Substituted-3-Pyrrolidyl α-Substituted Phenylacetates," Journal of Medicinal and Pharmaceutical Chemistry, 2(5):523-540 (1960).
CAPLUS Chemical Abstract for WO 02/04402 database accession No. 136:118468; published Jan. 17, 2002.
Patent Abstract of Japan for JP 56 079688; published Jun. 30, 1981.
Derwent Abstract for FR 2 155 927, WPI accession No. 1973-45844U.
International Search Report for WO 03/087094 (PCT. phase of the instant national stage application) dated Jan. 30, 2004.

* cited by examiner

*Primary Examiner*—Joseph K. McKane
*Assistant Examiner*—Yong Chu
(74) *Attorney, Agent, or Firm*—Finnegan, Henderson, Farabow, Garrett & Dunner, LLP

(57) ABSTRACT

New pyrrolidinium derivatives having the chemical structure of general formula (I)

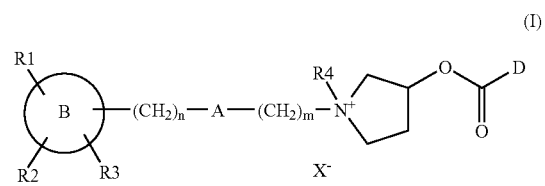

are disclosed; as well as processes for their preparation, pharmaceutical compositions comprising them and their use in therapy as antagonists of M3 muscarinic receptors.

23 Claims, No Drawings

PYRROLIDINIUM DERIVATIVES

This application is a national stage filing under 35 U.S.C. § 371 of International Application No. PCT/EP03/03786, filed on Apr. 11, 2003. This application claims the benefit of priority under 35 U.S.C. § 119 to Spanish Patent Application No. P200200889 filed on Apr. 16, 2002.

This invention relates to new therapeutically useful pyrrolidinium derivatives, to some processes for their preparation and to pharmaceutical compositions containing them.

The novel structures according to the invention are antimuscarinic agents with a potent and long lasting effect. In particular, these compounds show high affinity for M3 muscarinic receptors. This subtype of muscarinic receptor is present in glands and smooth muscle and mediates the excitatory effects of the parasympathetic system on glandular secretion and on the contraction of visceral smooth muscle (Chapter 6, Cholinergic Transmission, in H. P. Rang et al., Pharmacology, Churchill Livingstone, New York, 1995).

M3 antagonists are therefore known to be useful for treating diseases characterised by an increased parasympathetic tone, by excessive glandular secretion or by smooth muscle contraction (R. M. Eglen and S. S. Hegde, (1997), Drug News Perspect., 10(8):462–469).

Examples of this kind of diseases are respiratory disorders such as chronic obstructive pulmonary disease (COPD), bronchitis, bronchial hyperreactivity, asthma, cough and rhinitis; urological disorders such as urinary incontinence, pollakiuria, neurogenic or unstable bladder, cystospasm and chronic cystitis; gastrointestinal disorders such as irritable bowel syndrome, spastic colitis, diverticulitis and peptic ulceration; and cardiovascular disorders such as vagally induced sinus bradycardia (Chapter 7, Muscarinic Receptor Agonists and Antagonists, in Goodman and Gilman's The Pharmacological Basis of Therapeutics, 10th edition, McGraw Hill, New York, 2001).

The compounds of the invention can be used alone or in association with other drugs commonly regarded as effective in the treatment of these diseases. For example, they can be administered in combination with $\beta_2$-agonists, steroids, antiallergic drugs, phosphodiesterase IV inhibitors an/or leukotriene D4 (LTD4) antagonists for simultaneous, separate or sequential use in the treatment of a respiratory disease.

The new pyrrolidinium derivatives of the invention have the chemical structure of formula (I):

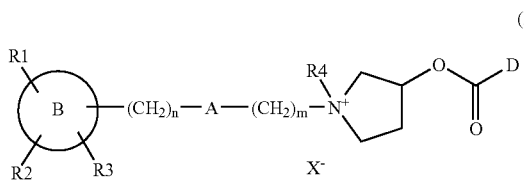

(I)

wherein

B is a phenyl, naphthalenyl, 5,6,7,8-tetrahydronaphthalenyl, benzo[1,3]dioxolyl or biphenyl group or a 5 to 10-membered heteroaromatic group containing one or more, for example 1, 2, 3 or 4, heteroatoms selected from N, O or S;

$R^1$, $R^2$ and $R^3$ each independently represent a hydrogen or halogen atom, or a hydroxy, phenyl, —$OR^5$, —$SR^5$, —$NR^5R^6$, —$NHCOR^5$, —$CONR^5R^6$, —CN, —$NO_2$, —$COOR^5$ or —$CF_3$ group, or a straight or branched, optionally substituted lower alkyl group;

or $R^1$ and $R^2$ together form an aromatic or alicyclic ring or a heterocyclic group;

$R^5$ and $R^6$ each independently represent a hydrogen atom, a straight or branched, optionally substituted lower alkyl group, or together form an alicyclic ring;

n is an integer from 0 to 4;

A represents a group selected from —$CH_2$—, —CH=$CR^7$—, —$CR^7$=CH—, —$CR^7R^8$—, —CO—, —O—, —S—, —S(O)—, —$S(O)_2$— and —$NR^7$—, wherein $R^7$ and $R^8$ each independently represent a hydrogen atom, a straight or branched, optionally substituted lower alkyl group, or together form an alicyclic ring;

m is an integer from 0 to 8;

$R^4$ represents a lower alkyl group;

D represents a group of formula i) or ii)

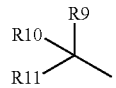

i)

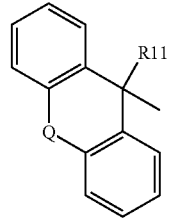

ii)

wherein $R^9$ represents a group selected from phenyl, 2-furyl, 3-furyl, 2-thienyl or 3-thienyl;

$R^{10}$ represent a group selected from phenyl, 2-furyl, 3-furyl, 2-thienyl, 3-thienyl or $C_3$–$C_7$ cycloalkyl;

and $R^{11}$ represents a hydrogen atom or a hydroxy, methyl, or —$CH_2OH$ group;

the cyclic groups represented by $R^9$ and $R^{10}$ being optionally substituted by one or two substituents selected from halogen, straight or branched, optionally substituted lower alkyl, hydroxy, optionally substituted lower alkoxy, nitro, cyano, —$CO_2R^{12}$ or —$NR^{2}R^{13}$, wherein $R^{12}$ and $R^{13}$ are identical or different and are selected from hydrogen and straight or branched, optionally substituted lower alkyl groups;

Q represents a single bond or a —$CH_2$—, —$CH_2$—$CH_2$—, —O—, —O—$CH_2$—, —S—, —S—$CH_2$— or —CH=CH— group;

$X^-$ represents a pharmaceutically acceptable anion of a mono or polyvalent acid;

including all individual stereoisomers and mixtures thereof;

with the proviso that in those compounds wherein B is phenyl, $R^9$ is unsubstituted phenyl, $R^{10}$ is unsubstituted phenyl or unsubstituted $C_3$–$C_7$ cycloalkyl, $R^{11}$ is hydrogen or hydroxy, the sequence —$(CH_2)_n$—A—$(CH_2)_m$— is not one of methylene, ethylene or propylene.

Further objectives of the present invention are to provide processes for preparing said compounds; pharmaceutical compositions comprising an effective amount of said compounds; the use of the compounds in the manufacture of a medicament for the treatment of diseases susceptible of being improved by antagonism of M3 muscarinic receptors;

and methods of treatment of diseases susceptible to amelioration by antagonism of M3 muscarinic receptors, which methods comprise the administration of the compounds of the invention to a subject in need of treatment.

Certain 3-pyrrolidinol esters, including some pyrrolidinium derivatives, which fall outside the scope of the present invention, have been disclosed in U.S. Pat. No. 2,956,062.

In the quaternary ammonium compounds of the present invention represented by formula (I), an equivalent of an anion ($X^-$) is associated with the positive charge of the N atom. $X^-$ may be an anion of various mineral acids such as, for example, chloride, bromide, iodide, sulphate, nitrate, phosphate, or an anion of an organic acid such as, for example formate, acetate, maleate, fumarate, citrate, oxalate, succinate, tartrate, malate, mandelate, trifluoroacetate, methanesulphonate and p-toluenesulphonate. $X^-$ is preferably an anion selected from chloride, bromide, iodide, sulphate, nitrate, formate, acetate, maleate, oxalate, succinate or trifluoroacetate. More preferably $X^-$ is chloride, bromide, trifluoroacetate, formate or methanesulphonate and still more preferably chloride, bromide, trifluoroacetate or methanesulphonate.

As used herein, an alkyl group can be straight or branched, and is typically a lower alkyl group. A lower alkyl group contains 1 to 8, preferably 1 to 6 and more preferably 1 to 4 carbon atoms. In particular it is preferred that such an alkyl group is represented by a methyl, ethyl, propyl, including i-propyl, or butyl including a n-butyl, sec-butyl and tert-butyl group.

Optionally substituted lower alkyl groups mentioned herein include straight or branched alkyl groups containing from 1 to 8, preferably from 1 to 6, more preferably from 1 to 4 carbon atoms as mentioned above, which may be unsubstituted or substituted in any position by one or more substituents, for example by 1, 2 or 3 substituents. When two or more substituents are present, each substituent may be the same or different. The substituent(s) are typically halogen atoms, preferably fluoride atoms, and hydroxy or alkoxy groups.

Alkoxy groups mentioned herein are typically lower alkoxy groups, that is groups containing from 1 to 8, preferably 1 to 6 and more preferably 1 to 4 carbon atoms, the hydrocarbon chain being branched or straight and optionally substituted in any position by one or more substituents, for example by 1, 2 or 3 substituents. When two or more substituents are present, each substituent may be the same or different. The substituent(s) are typically halogen atoms, most preferably fluoride atoms. Preferred optionally substituted alkoxy groups include methoxy, ethoxy, n-propoxy, i-propoxy, n-butoxy, sec-butoxy, tert-butoxy, trifluoromethoxy and difluoromethoxy.

Cycloalkyl groups and alicyclic groups mentioned herein, unless otherwise specified, typically contain from 3 to 8 carbon atoms, preferably from 3 to 6 carbon atoms. Cycloalkyl groups and alicyclic rings of 3 to 6 carbon atoms include cyclopropyl, cyclobutyl, cyclopentyl and cyclohexyl. Cycloalkyl groups containing from 3 to 7 carbon atoms include cycloalkyl groups of 3 to 6 carbon atoms and cycloheptyl.

As used herein an aromatic ring or group typically contains from 5 to 14, preferably 5 to 10 carbon atoms. Examples of aromatic groups include phenyl and naphthalenyl.

A heterocyclic or heteroaromatic group mentioned herein is typically a 5 to 10 membered group, such as a 5, 6 or 7 membered group, containing one or more heteroatoms selected from N, S and O. Typically, 1, 2, 3 or 4 heteroatoms are present, preferably 1 or 2 heteroatoms. A heterocyclic or heteroaromatic group may be a single ring or two or more fused rings wherein at least one ring contains a heteroatom. Examples of heterocyclic groups include piperidyl, pyrrolidyl, piperazinyl, morpholinyl, thiomorpholinyl, pyrrolyl, imidazolyl, imidazolidinyl, pyrazolinyl, indolinyl, isoindolinyl, pyridyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, quinuclidinyl, triazolyl, pyrazolyl, tetrazolyl and thienyl. Examples of heteroaromatic groups include pyridyl, thienyl, furyl, pyrrolyl, imidazolyl, benzothiazolyl, pyridinyl, pyrazolyl, pyrazinyl, pyrimidinyl, pyridazinyl, indolyl, indazolyl, purinyl, quinolyl, isoquinolyl, phthalazinyl, naphthyridinyl, quinoxalinyl, quinazolinyl, cinnolinyl, triazolyl and pyrazolyl.

As used herein a halogen atom includes a fluorine, chlorine, bromine or iodine atom, typically a fluorine, chlorine or bromine atom.

Preferred compounds of formula (I) are those wherein B represents a phenyl, pyrrolyl, thienyl, furyl, biphenyl, naphthalenyl, 5,6,7,8-tetrahydronaphthalenyl, benzo[1,3]dioxolyl, imidazolyl or benzothiazolyl group. Most preferably B represents a phenyl, thienyl or pyrrolyl group.

B may be unsubstituted or substituted with one, two or three groups ($R^1$ to $R^3$) which may be in any position on the ring.

In the preferred compounds of the invention $R^1$, $R^2$ and $R^3$ each independently represent a hydrogen or halogen atom, or a hydroxy, methyl, tert-butyl, —$CH_2OH$, 3-hydroxypropyl, —OMe, —$NMe_2$, —NHCOMe, —$CONH_2$, —CN, —$NO_2$, —COOMe or —$CF_3$ group. In the most preferred compounds $R^1$, $R^2$ and $R^3$ are hydrogen, fluorine, chlorine or hydroxy.

Typically B is unsubstituted or substituted with one group, for example when B is a phenyl group it may be substituted in the 2, 3 or 4 position. Examples of substituted phenyl groups which may represent B are tolyl including o-, m- and p-tolyl, 3-cyanophenyl, 2-, 3- and 4-hydroxyphenyl and 2-, 3- and 4-fluorophenyl.

Preferred compounds of formula (I) are those wherein n=0 or 1; m is an integer from 1 to 6, particularly 1, 2 or 3; and A represents a —$CH_2$—, —CH=CH—, —CO—, —NMe-, —O— or —S-group. Most preferred compounds are those wherein A is a —$CH_2$—, —CH=CH— or —O— group.

Further preferred compounds of formula (I) are those wherein the pyrrolidinium group is substituted on the nitrogen atom with a $C_1$–$C_4$ alkyl group and another group selected from 3-phenoxypropyl, 2-phenoxyethyl, 3-phenylallyl, phenethyl, 4-phenylbutyl, 3-phenylpropyl, 3-(2-hydroxyphenoxy)propyl, 3-(4-fluorophenoxy)propyl, 2-benzyloxyethyl, 3-pyrrol-1-ylpropyl, 2-thien-2-ylethyl, 3-thien-2-ylpropyl, 3-phenylaminopropyl, 3-(methylphenylamino) propyl, 3-phenylsulphanylpropyl, 3-tolyloxypropyl, 3-(2,4,6-trimethylphenoxy)propyl, 3-(2-tert-butyl-6-methylphenoxy)propyl, 3-(biphenyl-4-yloxy)propyl, 3-(5,6,7,8-tetrahydronaphthalen-2-yloxy)-propyl, 3-(naphthalen-2-yloxy)propyl, 3-(naphthalen-1-yloxy)propyl, 3-(2-chlorophenoxy)propyl, 3-(2,4-difluorophenoxy)propyl, 3-(3-trifluoromethylphenoxy)propyl, 3-(3-cyanophenoxy) propyl, 3-(4-cyanophenoxy)propyl, 3-(3-methoxyphenoxy) propyl, 3-(4-methoxyphenoxy)propyl, 3-(benzo[1,3]dioxol-5-yloxy)propyl, 3-(2-carbamoylphenoxy)propyl, 3-(3-dimethylaminophenoxy)propyl, 3-(4-nitrophenoxy)propyl, 3-(3-nitrophenoxy)propyl, 3-(4-acetylaminophenoxy)propyl, 3-(4-methoxycarbonylphenoxy)propyl, 3-[4-(3-hydroxypropyl)phenoxy]propyl, 3-(2-hydroxymethylphenoxy)propyl, 3-(3-hydroxymethylphenoxy)propyl, 3-(4-hydroxymethylphenoxy)propyl, 3-(2-hydroxyphenoxy)propyl, 3-(4-hydroxyphenoxy)propyl, 3-(3-hydroxyphenoxy)propyl, 4-oxo-4-thien-2-ylbutyl, 3-(1-methyl-[1H]-imidazol-2-ylsulphanyl)propyl, 3-(benzothiazol-2-yloxy)propyl, 3-benzyloxypropyl, 6-(4-phenylbutoxy)hexyl, 4-phenoxybutyl, 4-(4-fluorophenyl)-4-oxobutyl or 4-oxo-4-phenylbutyl.

Most preferred are those compounds wherein the pyrrolidinium group is substituted on the nitrogen atom with a $C_1$–$C_4$ alkyl group and another group selected from 3-phenoxypropyl, 2-phenoxyethyl, 3-phenylallyl, phenethyl, 3-phenylpropyl, 3-(3-hydroxyphenoxy)propyl, 3-(4-fluorophenoxy)propyl , 3-thien-2-ylpropyl, 4-oxo-4-thien-2-ylbutyl, 2-benzyloxyethyl, 3-o-tolyloxypropyl, 3-(3-cyanophenoxy)propyl, 3-(methylphenylamino)propyl, 3-phenylsulphanylpropyl, 4-oxo-4-phenylbutyl, 4-(4-fluorophenyl)-4-oxobutyl, 3-(2-chlorophenoxy)propyl, 3-(2,4-difluorophenoxy)propyl, 3-(4-methoxyphenoxy)propyl, 3-(benzo[1,3]dioxol-5-yloxy)propyl.

Examples of especially preferred compounds are those wherein the pyrrolidinium group is substituted on the nitrogen atom with a $C_1$–$C_4$ alkyl group and another group selected from 3-phenoxypropyl, 2-phenoxyethyl, 3-phenylallyl, phenethyl, 3-phenylpropyl, 3-(3-hydroxyphenoxy)propyl, 3-(4-fluorophenoxy)propyl, 4-(4-fluorophenyl)$_4$-oxobutyl or 3-thien-2-ylpropyl.

Further preferred compounds of formula (I) are those wherein D is a group of formula i), and wherein $R^9$ is a group selected from phenyl, 2-thienyl, 3-thienyl, 3-furyl or 2-furyl more preferably phenyl, 2-thienyl or 2-furyl; $R^{10}$ is a group selected from phenyl, 2-thienyl, 2-furyl, 3-furyl, 3-thienyl, cyclohexyl or cyclopentyl more preferably phenyl, 2-thienyl, cyclohexyl or cyclopentyl; and $R^{11}$ is a hydroxy group.

Also preferred are compounds of formula (I) wherein D is a group of formula ii), and wherein Q is a single bond or an oxygen atom and $R^{11}$ is a hydrogen atom or a hydroxy group.

The compounds of the present invention represented by formula (I) have at least two chiral centers: one at the carbon atom in position 3 of the pyrrolidinium ring and another at the N atom of the pyrrolidinium ring. Additionally, depending on the nature of group D they may also have an additional chiral center at the carbon atom of this group which is attached to the ester function. Each of these chiral centers may have R— or S— configuration. The single isomers and mixtures of the isomers fall within the scope of the invention.

Since the compounds have one or more chiral centers they may be obtained as pure isomers or as mixtures of the different enantioners or diastereomers.

In the present invention when no indication is given on the configuration of a chiral center, it is to be understood that reference is made to the mixture of all possible isomers at the corresponding chiral center.

When compounds with a specific configuration at a chiral center are meant, this is indicated in the name of the compound as follows:
  when the configuration at the chiral center is known, it is indicated by using the Cahn-Ingold-Prelog nomenclature attaching the letter R or S to the number specifying the position of the chiral center in the molecule.
  when the chiral center has a specific configuration which is however unknown, it is indicated by attaching an asterisk (*) to the number specifying the position of the chiral center in the molecule.

Particular compounds of the invention include:
3-(2-Hydroxy-2,2-dithien-2-ylacetoxy)-1-methyl-1-phenethylpyrrolidinium trifluoroacetate
3-(2-Hydroxy-2,2-dithien-2-ylacetoxy)-1-methyl-1-(2-phenoxyethyl)pyrrolidinium bromide
3-(2-Hydroxy-2,2-dithien-2-ylacetoxy)-1-methyl-1-(3-thien-2-ylpropyl)pyrrolidinium bromide
3-(2-Hydroxy-2,2-dithien-2-ylacetoxy)-1-methyl-1-(3-phenoxypropyl) pyrrolidinium bromide
3-(2-Hydroxy-2,2-dithien-2-ylacetoxy)-1-methyl-1-(3-phenylallyl)pyrrolidinium trifluoroacetate
3-(2-Hydroxy-2,2-dithien-2-ylacetoxy)-1-methyl-1-(4-oxo-4-thien-2-ylbutyl)pyrrolidinium trifluoroacetate
1-[4-(4-Fluorophenyl)-4-oxobutyl]-3-(2-hydroxy-2,2-dithien-2-ylacetoxy)-1-methylpyrrolidinium trifluoroacetate
1-Ethyl-3-(2-Hydroxy-2,2-dithien-2-ylacetoxy)-1-[3-(3-hydroxyphenoxy)propyl]pyrrolidinium trifluoroacetate
3-(2-Hydroxy-2,2-dithien-2-yl-acetoxy)-1-methyl-1-(3-pyrrol-1-ylpropyl)pyrrolidinium trifluoroacetate
3-(2-Hydroxy-2,2-dithien-2-ylacetoxy)-1-methyl-1-[6-(4-phenylbutoxy)hexyl]pyrrolidinium trifluoroacetate
1-(2-Benzyloxyethyl)-3-(2-cyclohexyl-2-fur-2-yl-2-hydroxyacetoxy)-1-methylpyrrolidinium trifluoroacetate
1-[3-(3-Cyanophenoxy)propyl]-3-(2-cyclohexyl-2-fur-2-yl-2-hydroxyacetoxy)-1-methylpyrrolidinium trifluoroacetate
3-(2-Cyclohexyl-2-fur-2-yl-2-hydroxyacetoxy)-1-methyl-1-[3-(naphthalen-1-yloxy)propyl]pyrrolidinium trifluoroacetate
3-(2-Cyclohexyl-2-fur-2-yl-2-hydroxyacetoxy)-1-methyl-1-[3-(methylphenylamino)propyl]pyrrolidinium trifluoroacetate
3-(2-Cyclohexyl-2-fur-2-yl-2-hydroxyacetoxy)-1-ethyl-1-(3-phenylsulphanylpropyl)pyrrolidinium trifluoroacetate
1-[3-(Benzothiazol-2-yloxy)propyl]-3-(2-cyclohexyl-2-fur-2-yl-2-hydroxyacetoxy)-1-methylpyrrolidinium trifluoroacetate
3-(2-Cyclopentyl-2-hydroxy-2-phenylacetoxy)-1-methyl-1-(3-phenoxypropyl)pyrrolidinium bromide
3-(2-Cyclopentyl-2-hydroxy-2-phenylacetoxy)-1-methyl-1-[3-(2,4,6-trimethylphenoxy)propyl]pyrrolidinium trifluoroacetate
1-[3-(2-Chlorophenoxy)propyl]-3-(2-cyclopentyl-2-hydroxy-2-phenylacetoxyl-1-methylpyrrolidinium trifluoroacetate
3-(2-Cyclopentyl-2-hydroxy-2-phenylacetoxy)-1-methyl-1-[3-(3-trifluoromethylphenoxy)propyl]pyrrolidinium trifluoroacetate
1-[3-(Biphenyl-4-yloxy)propyl]-3-(2-cyclopentyl-2-hydroxy-2-phenylacetoxy)-1-methylpyrrolidinium trifluoroacetate
3-(2-Cyclopentyl-2-hydroxy-2-phenylacetoxy)-1-[3-(2,4-difluorophenoxy)propyl]-1-methylpyrrolidinium trifluoroacetate
3-(2-Cyclopentyl-2-hydroxy-2-phenylacetoxy)-1-ethyl-1-[3-(4-methoxyphenoxy)propyl]pyrrolidinium trifluoroacetate
3-(2-Cyclopentyl-2-hydroxy-2-phenylacetoxy)-1-methyl-1-[3-(5,6,7,8-tetrahydronaphthalen-2-yloxy)propyl]pyrrolidinium trifluoroacetate
3-(2-Cyclopentyl-2-hydroxy-2-phenylacetoxy)-1-methyl-1-[3-(1-methyl-1H-imidazol2-ylsulphanyl)propyl]pyrrolidinium trifluoroacetate 1-Methyl-1-phenethyl-3-(9H-xanthen-9-ylcarbonyloxy)pyrrolidinium bromide
1-Methyl-1-(3-phenoxypropyl)-3-(9H-xanthen-9-ylcarbonyloxy)pyrrolidinium bromide
1-[3-(Benzo[1,3]dioxol-5-yloxy)propyl]-1-methyl-3-(9H-xanthen-9-ylcarbonyloxy)pyrrolidinium trifluoroacetate
1-[3-(2-Carbamoylphenoxy)propyl]-1-methyl-3-(9H-xanthen-9-ylcarbonyloxy)pyrrolidinium trifluoroacetate
1-[3-(3-Dimethylaminophenoxy)propyl]-1-methyl-3-(9H-xanthen-9-ylcarbonyloxy)pyrrolidinium trifluoroacetate
1-[3-(4-Acetylaminophenoxy)propyl]-1-methyl-3-(9H-xanthen-9-ylcarbonyloxy)pyrrolidinium trifluoroacetate
1-[3-(4-Methoxycarbonylphenoxy)propyl]-1-methyl-3-(9H-xanthen-9-ylcarbonyloxy)pyrrolidinium trifluoroacetate
1-Methyl-1-[3-(4-nitrophenoxy)propyl]-3-(9H-xanthen-9-ylcarbonyloxy)pyrrolidinium trifluoroacetate
1-[3-(4-Hydroxymethylphenoxy)propyl]-1-methyl-3-(9H-xanthen-9-ylcarbonyloxy)pyrrolidinium trifluoroacetate
3-(2-Hydroxy-2,2-dithien-2-ylacetoxy)-1-[3-(3-hydroxyphenoxy)propyl]-1-methylpyrrolidinium formate
1-[3-(4-Fluorophenoxy)propyl]-3-(2-hydroxy-2,2-dithien-2-ylacetoxy)-methylpyrrolidinium chloride
3-(2-Hydroxy-2,2-dithien-2-ylacetoxy)-1-methyl-1-(3-phenylpropyl)pyrrolidinium bromide
1-Methyl-1-(3-o-tolyloxypropyl)-3-[(9H-xanthen-9-ylcarbonyl)oxy]pyrrolidinium bromide
3-{[(9-hydroxy-9H-fluoren-9-yl)carbonyl]oxy}-methyl-1-(4-oxo-4-phenylbutyl)pyrrolidinium formate
3-(2-Cyclohexyl-2-fur-2-yl-2-hydroxyacetoxy)-1-ethyl-1-(3-phenylsulfanylpropyl)pyrrolidinium bromide
Particular mixtures of isomers of the compounds of the invention include:
(3R)-3-(2-Hydroxy-2,2-dithien-2-ylacetoxy)-1-methyl-1-phenethylpyrrolidinium bromide
(3S)-3-(2-Hydroxy-2,2-dithien-2-ylacetoxy)-1-methyl-1-phenethylpyrrolidinium bromide
(3R)-3-(2-Hydroxy-2,2-dithien-2-ylacetoxy)-1-methyl-1-(2-phenoxyethyl)pyrrolidinium bromide
(3S)-3-(2-Hydroxy-2,2-dithien-2-ylacetoxy)-1-methyl-1-(2-phenoxyethyl)pyrrolidinium bromide
(3R)-3-2-Hydroxy-2,2-dithien-2-ylacetoxy)-1-methyl-1-(3-thien-2-ylpropyl)pyrrolidinium bromide
(3R)-3-(2-Hydroxy-2,2-dithien-2-ylacetoxy)-methyl-1-(3-phenoxypropyl)pyrrolidinium bromide
(3S)-(2-Hydroxy-2,2-dithien-2-ylacetoxy)-methyl-1-(3-phenoxypropyl)pyrrolidinium bromide
(3R)-3-[(2R)-2-Cyclohexyl-2-fur-2-yl-2-hydroxyacetoxy]-1-ethyl-1-(3-phenylsulphanylpropyl)pyrrolidinium trifluoroacetate
(3S)-3-[(2R)-2-Cyclohexyl-2-fur-2-yl-2-hydroxyacetoxy]-1-ethyl-1-(3-phenylsulphanylpropyl)pyrrolidinium trifluoroacetate
(3R)-3-[(2R)-2-Cyclopentyl-2-hydroxy-2-phenylacetoxy]-1-methyl-1-(3-phenoxypropyl)pyrrolidinium bromide
(3S)-3-[(2R)-2-Cyclopentyl-2-hydroxy-2-phenylacetoxy]-1-methyl-1-(3-phenoxypropyl)pyrrolidinium bromide
(3R)-3-[(2S-2-Cyclopentyl-2-hydroxy-2-phenylacetoxy]-1-methyl-1-(3-phenoxypropyl)pyrrolidinium bromide
(3S)-3-[(2S-2-Cyclopentyl-2-hydroxy-2-phenylacetoxy]-1-methyl-1-(3-phenoxypropyl)pyrrolidinium bromide
(3R)-1-Methyl-1-phenethyl-3-(9H-xanthen-9-ylcarbonyloxy)pyrrolidinium bromide
(3S)-1-Methyl-1-phenethyl-3-(9H-xanthen-9-ylcarbonyloxy)pyrrolidinium bromide
(3S)-3-(2-Hydroxy-2,2-dithien-2-ylacetoxy)-1-[3-(3-hydroxyphenoxy)propyl]-1-methylpyrrolidinium formate
(3R)-3-{[(9-hydroxy-9H-fluoren-9-yl)carbonyl]oxy}1-methyl-1-(4-oxo-4-phenylbutyl)pyrrolidinium formate
(3R)-3-(2-Hydroxy-2,2-dithien-2-ylacetoxy)-1-methyl-1-(4-oxo-4-thien-2-ylbutyl)pyrrolidinium chloride
(3R)-1-[4-(4-Fluorophenyl)-4-oxobutyl]-3-(2-hydroxy-2,2-dithien-2-ylacetoxy)-1-methylpyrrolidinium formate
(3R)-1-[3-(3-Cyanophenoxy)propyl]-3-(2-cyclohexyl-2-fur-2-yl-2-hydroxyacetoxy)-1-methylpyrrolidinium formate
(3R)-3-(2-Cyclohexyl-2-fur-2-yl-2-hydroxyacetoxy)-1-methyl-1-[3-(naphthalen-1-yloxy)propyl]pyrrolidinium formate
(3R)-3-(2-Cyclohexyl-2-fur-2-yl-2-hydroxyacetoxy)-1-methyl-1-[3-(methylphenylamino)propyl]pyrrolidinium chloride
(3R)-1-[3-(Benzothiazol-2-yloxy)propyl]-3-(2-cyclohexyl-2-fur-2-yl-2-hydroxyacetoxy)-1-methylpyrrolidinium chloride
(3R)-1-[3-(Biphenylyloxy)propyl]-3-[(2R)-2-cyclopentyl-2-hydroxy-2-phenylacetoxy]-1-methylpyrrolidinium chloride
(3R)-3-[(2R)-2-Cyclopentyl-2-hydroxy-2-phenylacetoxy]-1-methyl-[3-(5,6,7,8-tetrahydronaphthalen-2-yloxy)propyl]pyrrolidinium bromide
(3R)-3-[(2R)-2-Cyclopentyl-2-hydroxy-2-phenylacetoxy]-1-methyl-1-[3-(1-methyl-1H-imidazol-2-ylsulfanyl)propyl]pyrrolidinium chloride
(3R)-1-[3-(2-Chlorophenoxy)propyl]-3-[(2R-2-cyclopentyl-2-hydroxy-2-phenylacetoxy]-1-methylpyrrolidinium chloride
3-[(2R-2-Cyclopentyl-2-hydroxy-2-phenylacetoxy]-1-ethyl-1-[3-(4-methoxyphenoxy)propyl]pyrrolidinium bromide
(3R)-1-(2-Benzyloxyethyl)-3-(2-cyclohexyl-2-fur-2-yl-2-hydroxyacetoxy)-1-methylpyrrolidinium bromide
Individual isomers of the compounds of the invention include:
(1*,3R)-3-(2-Hydroxy-2,2-dithien-2-ylacetoxy)-1-methyl-1-phenethylpyrrolidinium bromide (diastereomer 1)
(1*,3R)-3-(2-Hydroxy-2,2-dithien-2-ylacetoxy-1-methyl-1-phenethylpyrrolidinium bromide (diastereomer 2)
(1*,3R-3-(2-Hydroxy-2,2-dithien-2-ylacetoxy)-1-methyl-1-(2-phenoxyethyl)pyrrolidinium bromide (diastereomer 1)
(1*,3R)-3-(2-Hydroxy-2,2-dithien-2-ylacetoxy)-1-methyl-1-(2-phenoxyethyl)pyrrolidinium bromide (diastereomer 2)
(1*,3S)-3-(2-Hydroxy-2,2-dithien-2-ylacetoxy)-1-methyl-1-(2-phenoxyethyl)pyrrolidinium bromide (diastereomer 1)
(1*,3S)-3-(2-Hydroxy-2,2-dithien-2-ylacetoxy)-1-methyl-1-(2-phenoxyethyl)pyrrolidinium bromide (diastereomer 2)
(1*,3R)-3-(2-Hydroxy-2,2-dithien-2-ylacetoxy)-1-methyl-1-(3-phenoxypropyl)pyrrolidinium bromide (diastereomer 1)
(1*,3R)-3-(2-Hydroxy-2,2-dithien-2-ylacetoxy)-1-methyl-1-(3-phenoxypropyl)pyrrolidinium bromide (diastereomer 2)
(1*,3S)-3-[(2R)-2-Cyclopentyl-1-hydroxy-2-phenylacetoxy]-1-methyl-1-(3-phenoxypropyl)pyrrolidinium bromide (diastereomer 1)
(1*,3S)-3-[(2R)-2-Cyclopentyl-2-hydroxy-2-phenylacetoxy]-methyl-1-(3-phenoxypropyl)pyrrolidinium bromide (diastereomer 2)
(1*,3R)-1-Methyl-1-phenethyl-3-(9H-xanthen-9-ylcarbonyloxy)pyrrolidinium bromide (diastereomer 1)
(1*,3R)-1-Methyl-1-phenethyl-3-(9H-xanthen-9-ylcarbonyloxy)pyrrolidinium bromide (diastereomer 2)
(1*,3R)-3-(2-Hydroxy-2,2-dithien-2-ylacetoxy)-1-methyl-1-(3-phenylallyl)pyrrolidinium bromide (diastereomer 1)

(1*,3R)-3-(2-Hydroxy-2,2-dithien-2-ylacetoxy)-1-methyl-1-(3-phenylallyl)pyrrolidinium bromide (diastereomer 2)
(1*,3R)-1-[4-(4-Fluorophenyl)-4-oxobutyl]-3-(2-hydroxy-2,2-dithien-2-ylacetoxy)-1-methylpyrrolidinium chloride (diastereomer 1)
(1*,3S)-1-[3-(4-Fluorophenoxy)propyl]-3-(2-hydroxy-2,2-dithien-2-ylacetoxy)-1-methylpyrrolidinium chloride (diastereomer 1)
(1*,3S)-1-[3-(4-Fluorophenoxy)propyl]-3-(2-hydroxy-2,2-dithien-2-ylacetoxy)-1-methylpyrrolidinium chloride (diastereomer 2)
(1*,3S-3-(2-Hydroxy-2,2-dithien-2-ylacetoxy)-1-methyl-1-(3-phenylpropyl)pyrrolidinium bromide (diastereomer 1)
(1*,3S)-3-(2-Hydroxy-2,2-dithien-2-ylacetoxy)-1-methyl-1-(3-phenylpropyl)pyrrolidinium bromide (diastereomer 2)
(1*,3R)-3-[(2R)-2-Cyclopentyl-2-hydroxy-2-phenylacetoxy]-1-methyl-1-(3-phenoxypropyl)pyrrolidinium bromide (diastereomer 1)
(1*,3R)-3-[(2R)-2-Cyclopentyl-2-hydroxy-2-phenylacetoxy]-1-methyl-1-(3-phenoxypropyl)pyrrolidinium bromide (diastereomer 2)
(1*,3R)-1-[3-(Benzo[1,3]dioxol-5-yloxy)propyl]-1-methyl-3-[(9H-xanthen-9-ylcarbonyl)oxy]pyrrolidinium bromide (diastereomer 1)
(1*,3R)-1-[3-(Benzo[1,3]dioxol-5-yloxy)propyl]-1-methyl-3-[(9H-xanthen-9-ylcarbonyl)oxy]pyrrolidinium bromide (diastereomer 2)
(1*,3S)-1-Methyl-1-(3-o-tolyloxypropyl)-3-[(9H-xanthen-9-ylcarbonyl)oxy]pyrrolidinium bromide (diastereomer 1)
(1*,3S)-1-Methyl-1-(3-o-tolyloxypropyl)-3-[(9H-xanthen-9-ylcarbonyl)oxy]pyrrolidinium bromide (diastereomer 2)
(1*,3R)-1-[3-(Biphenyl-4-yloxy)propyl]-3-[(2R)-2R)-cyclopentyl-2-hydroxy-2-phenylacetoxy]-1-methylpyrrolidinium chloride (diastereomer 1).
(1*,3R)-1-[3-(Biphenyl-4-yloxy)propyl]-3-[(2R)-2-cyclopentyl-2-hydroxy-2-phenylacetoxy]-1-methylpyrrolidinium chloride (diastereomer 2).
(1*,3R)-3-[(2R)-2-Cyclopentyl-2-hydroxy-2-phenylacetoxy]-1-methyl-1-[3-(5,6,7,8-tetrahydronaphthalen-2-yloxy)propyl]pyrrolidinium bromide (diastereomer 1).
(1*,3R-3-[(2R)-2-Cyclopentyl-2-hydroxy-2-phenylacetoxy]-1-methyl-1-[3-(5,6,7,8-tetrahydronaphthalen-2-yloxy)propyopyrrolidinium bromide (diastereomer 2).

In accordance with another embodiment, the present invention provides processes for preparing the novel pyrrolidinium derivatives of formula (I). These compounds may be prepared following two different procedures, illustrated below as method (a) and method (b).

Following method (a), the compounds of formula (I) are obtained by reaction of an alkylating agent of formula R4-W with intermediates of formula (II).

Method a

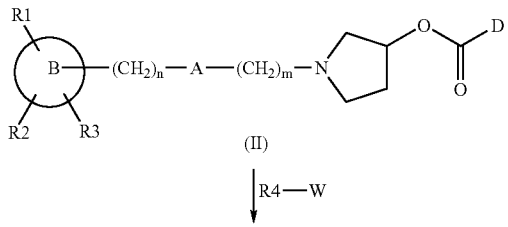

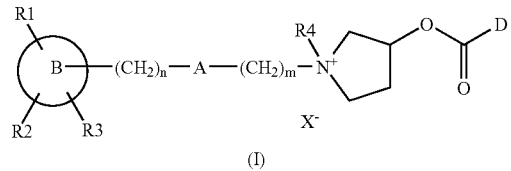

Following method (b) the compounds of formula (I) are prepared by reaction of an alkylating agent of formula (IV) with intermediates of formula (III).

Method b

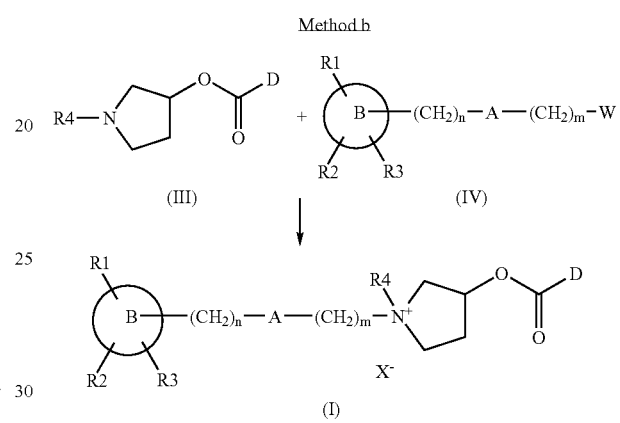

In formulae (I), (II), (III) and (IV), m, n, A, B, D, R1, R2, R3 and R4 and X⁻ are as defined above.

In formulae (IV) and R4-W, W represents any suitable leaving group, such a group X as defined above for the compounds of formula (I). Preferably, W represents a group X. When W represents a group other than X, the quaternary ammonium salt of formula (I) is produced from the product of method (a) or (b) by an exchange reaction according to standard methods to replace the anion W⁻ with the desired anion X⁻.

Methods (a) and (b) may be carried out by known experimental procedures in conventional synthesis, or using solid phase extraction methodologies, which allow the parallel preparation of several compounds.

The diastereomers of compounds of formula (I) may be separated by conventional methods, for example by chromatography or crystallisation.

The intermediates of formula (II) used in method (a) may be prepared by reaction of a compound of formula (V) with a compound of formula (VI) as shown in method (c) below Method c

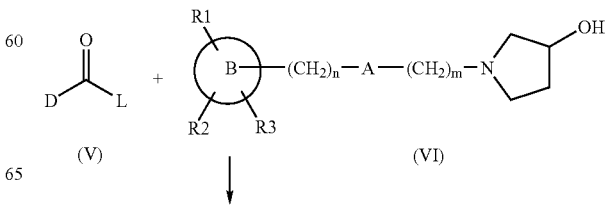

-continued

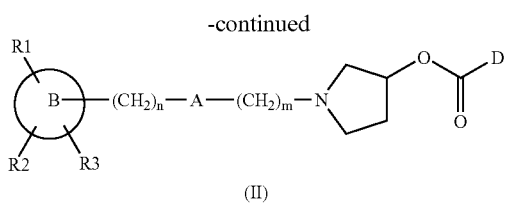

(II)

In formulae (II), (V) and (VI), m, n, A, B, D, R1, R2 and R3 are as defined above.

The pyrrolidinol esters of formula (II) may be converted to pharmaceutically acceptable salts by methods known in the art. Typically, an ester of formula (II) is treated with an inorganic or organic acid such as oxalic, fumaric, maleic, tartaric, succinic or hydrochloric acid.

The pyrrolidinol esters of formula (II) having one or more asymmetric carbons, include all the possible stereoisomers, single isomers and mixtures of isomers.

The diastereomers of compounds of formula (II) may be separated by conventional methods, for example by chromatography or crystallisation. Certain compounds of formula (II) are novel and fall under the scope of the present invention. In particular:

2-Hydroxy-2,2-dithien-2-ylacetic acid (3R)-1-(2-phenoxyethyl)pyrrolidin-3-yl ester 2-Hydroxy-2,2-dithien-2-ylacetic acid (3R)-1-(3-phenoxypropyl)pyrrolidin-3-yl ester 2-Hydroxy-2,2-dithien-2-ylacetic acid (3R)-1-(3-thien-2-ylpropyl)pyrrolidin-3-yl ester 2-Hydroxy-2,2-dithien-2-ylacetic acid (3R)-1-phenethylpyrrolidin-3-yl ester The compounds of formula (III), used in method (b), may be prepared by reaction of a compound of formula (V) with a compound of formula (VII) as described in method (d), illustrated below.

Method d

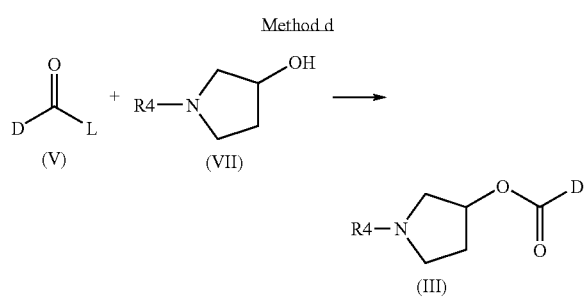

In the compounds of formulae (V), (III), and (VII), D and R4 are as described above for compounds of formula (I); and L in formula (V) represents a leaving group. For example, L may be a chlorine atom, an imidazol-1-yl group or a lower alkoxy group, such as a methoxy group.

The intermediates of formula (V) may be prepared by methods described in the literature as shown in the experimental section below.

The pyrrolidinol esters of formula (III) having one or more asymmetric carbons, include all the possible stereoisomers, single isomers and mixtures of stereoisomers. The diastereomers of compounds of formula (III) may be separated by conventional methods, for example by chromatography or crystallisation.

The compounds of formula (VI), described in method (c), may be prepared by reaction of an alkylating agent of formula (IV), wherein W is an halogen or a sulphonate ester, with the corresponding pyrrolidinol of formula (VIII), as illustrated in method (e) below.

Method e

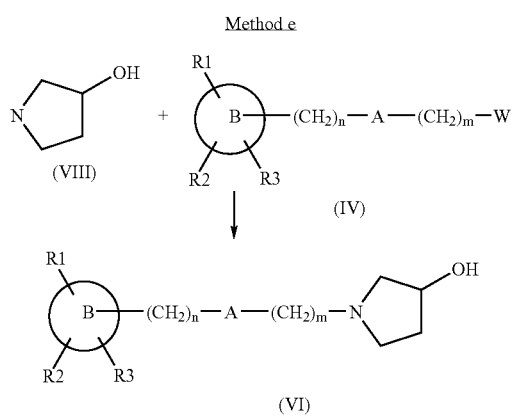

In formulae (IV) and (VI) m, n, A, B, R1, R2, R3 and W are as defined above.

Certain compounds of formula (VI) are novel and fall within the scope of the present invention. In particular:

(3R)-1-(3-phenoxypropyl)pyrrolidin-3-ol
(3R)-1-(3-thien-2-ylpropyl)pyrrolidin-3-ol Those compounds of formula (VII), described in method (d), which are not commercially available may be prepared by synthesis according to standard methods, for example by reaction of a compound of formula (VIII) with the corresponding alkylating agent, or by reaction of a compound of formula (VIII) with the corresponding aldehyde and a reductive agent. A particular example is described as method (f) in the experimental part.

Examples of compounds of formula (VIII) which are commercially available are pyrrolidin-3-ol, (3R)-pyrrolidin-3-ol, (3S)-pyrrolidin-3-ol.

Those compounds of formula (IV), which are not commercially available have been prepared by synthesis according to standard methods. For example, compounds wherein n is 0 and A is one of —O—, —S— or —NR$^7$, wherein R$^7$ is as defined above, were obtained by reaction of the corresponding alcohol, thiol or amine derivative or its sodium or potassium salt with an alkylating agent of formula Y—(CH$_2$)$_m$—W, wherein W is as defined above and Y may be a halogen atom or a sulphonate ester. Other examples are compounds of formula (IV), wherein n is at least 1, which were synthesised from the corresponding alcohol derivative of formula (IX) by methods well known in the art.

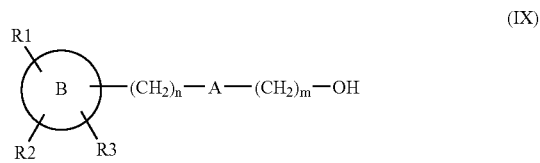

The following preparation examples are intended to illustrate, but no to limit the experimental procedures described above.

Method (a). Preparation of compounds of formula (I)
Method (b). Preparation of compounds of formula (I)
Methoc (c). Preparation of compounds of formula (II)
Method (d). Preparation of compounds of formula (III)
Method (e). Preparation of compounds of formula (VI)
Method (f). Preparation of compounds of formula (VII)

The structures of the obtained compounds were confirmed by $^1$H-NMR and MS. The NMR spectra were recorded using a Varian 300 MHz or a Bruker DPX-250 instrument. Chemical shifts are expressed as parts per million (δ) from the internal reference tetramethylsilane. The purity of the compounds was determined by HPLC, using reverse phase chromatography on a Waters instrument. Optical rotations were obtained using a PERKIN-ELMER 241 MC Polarimeter and molecular ions were produced by electrospray ionisation mass spectrometry on a Hewlett Packard instrument.

Semi-preparative HPLC-MS experiments were performed on a Gilson instrument equipped with a binary pump (Gilson piston pump 321); a vacuum degasser (Gilson 864); an injector-fraction collector (Gilson liquid handler 215); two injection modules, analytical and preparative (Gilson 819); a valve (Gilson Valvemate 7000); a 1/1000 splitter (Acurate by LC Packings); a make-up pump (Gilson 307); a diode array detector (Gilson 170) and a MS detector (a Thermoquest Finnigan aQa, a quadrupole mass spectrometer with ES an APCI ionisation modes). The HPLC-MS instrument was controlled by an IBM PC.

Method (a)

EXAMPLE 6

Preparation of (3R)-3-(2-Hydroxy-2,2-dithien-2-ylacetoxy)-1-methyl-1-(3-thien-2-ylpropyl)pyrrolidinium bromide 0.3 g (0.00069 mol) of 2-Hydroxy-2,2-dithien-2-ylacetic acid (3R)-1-(3-thien-2-ylpropyl)pyrrolidin-3-yl ester (Intermediate 1-3) were dissolved in 4 ml of acetonitrile and 6 ml of CHCl$_3$. To this solution 3.45 ml (0.00345 mol) of a 1 M solution of methyl bromide in acetonitrile were added. After stirring the mixture at room temperature under N$_2$ atmosphere during 24 h, the solvents were evaporated. Ether was added to the residue and the mixture stirred to obtain a solid. This solid was treated with ether several times, filtered and washed with ether. The yield was 0.34 g (93.2%) of the title compound as a mixture of two stereoisomers.

$^1$H-NMR: mixture of diastereomers 55:45.
$^1$H-NMR (DMSO-d$_6$): δ 1.95–2.20 (m, 3H), 2.60–2.80 (m, 2H), 2.80–2.90 (m, 1H), 2.94 and 3.10 (s, 3H), 3.20–3.45 (m, 2H), 3.45–3.95 (m, 4H), 5.52 (m, 1H), 6.90–7.05 (m, 4H), 7.10–7.20 (m, 2H), 7.37 (m, 1H), 7.40–7.55 (m, 3H).
MS [M−Br]$^+$: 448

EXAMPLE 9

Preparation of (1*,3R)-3-(2-Hydroxy-2,2-dithien-2-ylacetoxy)-1-methyl-1-(3-phenoxypropyl)pyrrolidinium bromide (diastereomer 1)

EXAMPLE 10

Preparation of (1*,3R)-3-(2-Hydroxy-2,2-dithien-2-ylacetoxy)-1-methyl-1-(3-phenoxypropyl)pyrrolidinium bromide (diastereomer 2)

Following the process described in Example 6, 1.6 g of (3R)-3-(2-Hydroxy-2,2-dithien-2-ylacetoxy)-1-methyl-1-(3-phenoxypropyl)pyrrolidinium bromide, mixture of two stereoisomers, (compound described in Example 8) were prepared from 2-Hydroxy-2,2-dithien-2-ylacetic acid (3R)-1-(3-phenoxypropyl)pyrrolidin-3-yl ester, Intermediate 1-2, and a 1M solution of methyl bromide in acetonitrile. The resulting compound was purified by chromatography on silica gel performing a gradient elution using chloroform plus isopropanol (50→100%) as eluent. Appropriate fractions were combined and evaporated to give the two title compounds. The structure was confirmed by $^1$H-NMR.

Diastereomer 1 (first eluted diastereomer), 0.628 g (80.1% based on single isomer) were obtained.
m.p.: 86.2–89.6° C.
$^1$H-NMR: diastereomer 1 (diastereomer 2 not observed)
$^1$H-NMR (DMSO-d$_6$): δ 2.10–2.30 (m, 3H), 2.65–2.80 (m, 1H), 3.0 (s, 3H), 3.50–3.65 (m, 3H), 3.70–3.85 (m, 2H), 3.85–3.95 (m, 1H), 4.05 (m, 2H), 5.54 (m, 1H), 6.90–7.05 (m, 5H), 7.10–7.20 (m, 2H), 7.25–7.35 (m, 2H), 7.50–7.55 (m, 3H).
MS [M−Br]$^+$: 458

(* Configuration not assigned)

Diastereomer 2 (second eluted diastereomer) 0.559 g (71.3% based on single isomer).
m.p.: 87.1–89.0° C.
$^1$H-NMR: diastereomer 2 (diastereomer 1 not observed)
$^1$H-NMR (DMSO-d$_6$): δ 2.05–2.30 (m, 3H), 2.65–2.80 (m, 1H), 3.15 (s, 3H), 3.40–3.55 (m, 2H), 3.55–3.80 (m, 3H), 3.95 (m, 3H), 5.55 (m, 1H), 6.90–7.05 (m, 5H), 7.05–7.20 (m, 2H), 7.30–7.40 (m, 2H), 7.45–7.50 (m, 3H).
MS [M−Br]$^+$: 458

(* Configuration not assigned)

Method (b)

EXAMPLE 7

Preparation of 3-(2-Hydroxy-2,2-dithien-2-ylacetoxy)-1-methyl-1-(3-phenoxypropyl)pyrrolidinium bromide.

0.66 g (0.002 mol) of 2-hydroxy-2,2-dithien-2-ylacetic acid 1-methylpyrrolidin-3-yl ester (Intermediate I-7) were dissolved in 9 ml of CHCl$_3$ and 6 ml of acetonitrile. 1.6 ml of (3-bromopropoxy)benzene (2.15 g, 0.01 mol) were added and the mixture was stirred during 72 hours at room temperature under N$_2$ atmosphere. Solvents were evaporated. Ether was added to the residue and the mixture stirred to obtain a solid. The solid was treated with ether several times, filtered and washed with ether. The yield was 0.75 g (69.4%) of the title compound as a mixture of four stereoisomers.
mp: 55.3–56.8° C.
$^1$H-NMR: mixture of diastereomers 56:44
$^1$H-NMR (DMSO-d$_6$): δ 2.05–2.30 (m, 3H), 2.60–2.80 (m, 1H), 2.96 and 3.12 (s, 3H), 3.40–3.50 (m, 1H), 3.50–3.82 (m, 4H), 3.85–4.0 (m, 2H), 4.0–4.10 (m, 1H), 5.52 (m, 1H), 6.90–7.01 (m, 5H), 7.10–7.15 (m, 2H), 7.25–7.35 (m, 2H), 7.42–7.52 (m, 3H)
MS [M−Br]$^+$: 458

EXAMPLE 4

Preparation of (1*,3R)-3-(2-Hydroxy-2,2-dithien-2-ylacetoxy)-1-methyl-1-(2-phenoxyethyl)pyrrolidinium bromide (diastereomer 1)

EXAMPLE 5

Preparation of (1*,3R)-3-(2-Hydroxy-2,2-dithien-2-ylacetoxy)-1-methyl-1-(2-phenoxyethyl)pyrrolidinium bromide (diastereomer 2)

2 g (0.00618 mol) of 2-hydroxy-2,2-dithien-2-ylacetic acid (3R)-1-methylpyrrolidin-3-yl ester (Intermediate I-5) were dissolved in 40 ml of THF and 1.86 g (0.00927 mol) of (2-bromoethoxy)benzene were added. The mixture was refluxed during 81 hours and stirred 64 hours at room temperature. During this process 2.46 g more of (2-bromoethoxy)benzene (0.0122 mol), in several portions, were added. After this time the reaction mixture was filtered and the solid obtained was washed with THF and ether. This solid (1.5 g) was treated with THF at reflux temperature during 30 min., filtered without cooling, and washed with THF and ether to give 0.850 g (52.5%, based on single isomer) of diastereomer 1.

The mother liquors of the first filtration were refluxed for a further 40 hours. The solid formed (diastereomer 1) was filtered, and the solution obtained was diluted with ether to give an oily residue. Solvents were poured off and the oily residue was dissolved in $CHCl_3$. This solution was evaporated to give 801 mg of a brown foam that was purified by chromatography on silica gel using $CHCl_3$/isopropanol (50:50) as eluent. Appropriate fractions were combined and evaporated to give 0.47 g (29% based on single isomer) of diastereomer 2.

Diastereomer 1. (First obtained diastereomer)
mp: 198.8–199.4° C.
$^1$H-NMR, diastereomer 1, 95:5.
$^1$H-NMR (DMSO-$d_6$): δ 2.10–2.25 (m, 1H), 2.65–2.82 (m, 1H), 3.20 (s, 3H), 3.60–3.90 (m, 5H), 3.95–4.05 (m, 1H), 4.38 (m, 2H), 5.56 (m, 1H), 6.95–7.05 (m, 5H), 7.10–7.20 (m, 2H), 7.30–7.42 (m, 2H), 7.45–7.60 (m, 3H).
MS [M−Br]$^+$: 444

(* Configuration not assigned)
Diastereomer 2. (Second obtained diastereomer)
m.p.: 85.9–87.6° C.
$^1$H-NMR: diastereomer 2, 95:5
$^1$H-NMR (DMSO-$d_6$): δ 2.10–2.25 (m, 1H), 2.65–2.85 (m, 1H), 3.04 (s, 3H), 3.62–3.72 (m, 1H), 3.78–3.90 (m, 4H), 3.97–4.04 (m, 1H), 4.45 (m, 2H), 5.55 (m, 1H), 6.98–7.03(m, 5H), 7.12–7.16 (m, 2H), 7.32–7.37 (m, 2H), 7.50–7.52 (m, 3H).
MS [M−Br]$^+$: 444

(* Configuration not assigned)

EXAMPLE 11

Preparation of (1*,3R)-1-Methyl-1-phenethyl-3-(9H-xanthen-9-ylcarbonyloxy)pyrrolidinium bromide (diastereomer 1)

EXAMPLE 12

Preparation of (1*,3R)-1-Methyl-1-phenethyl-3-(9H-xanthen-9-ylcarbonyloxy)pyrrolidinium bromide (diastereomer 2)

0.7 g (0.00226 mol) of 9H-Xanthene-9-carboxylic acid (3R)-1-methylpyrrolidin-3-yl ester (Intermediate I-8) were dissolved in 15 ml of THF and 0.63 g (0.46 ml, 0.0034 mol) of (2-bromoethyl)benzene were added. The mixture was refluxed during 96 hours and stirred 72 hours at room temperature. During this process 1.26 g more of (2-bromoethyl)benzene (0.92 ml, 0.0068 mol), in several portions, were added. After this time the reaction mixture was filtered and the solid obtained was washed with THF and ether. The yield was 0.301 g (53.7%, based on single isomer) of the diastereomer 1. The structure was confirmed by $^1$H-NMR.

The mother liquors were evaporated and the oily residue (0.450 g) was purified by chromatography on silica gel performing a gradient elution using chloroform plus isopropanol (25→85%) as eluent. Appropriate fractions were combined and evaporated to give 0.193 g (34.5% based on single isomer) of the diastereomer 2.

Diastereomer 1. (First obtained diastereomer)
mp: 232.3–233.1° C.
HPLC: diastereomer 1, 92.5:7.5
$^1$H-NMR (DMSO-$d_6$): δ2.0–2.15 (m, 1H), 2.55–2.70 (m, 1H), 3.0 (s, 3H), 3.0–3.10 (m, 2H), 3.45–3.75 (m, 5H), 3.85–3.92 (m, 1H), 5.30 (s, 1H), 5.36 (m, 1H), 7.10–7.50 (m, 13H).
MS [M−Br]$^+$: 414

(* Configuration not assigned)
Diastereomer 2. (Second obtained diastereomer)
mp: 79.6–81.2° C.
HPLC: diastereomer 2, 98.8:1.2
$^1$H-NMR (DMSO-$d_6$): δ 2.0–2.10 (m, 1H), 2.55–2.70 (m, 1H), 3.0–3.10 (m, 2H), 3.17 (s, 3H), 3.45–3.55 (m, 2H), 3.55–3.75 (m, 3H), 3.85–3.92 (m, 1H), 5.24 (s, 1H), 5.38 (m, 1H), 7.0–7.15 (m, 4H), 7.25–7.50 (m, 9H).
MS [M−Br]$^+$: 414

(* Configuration not assigned)

EXAMPLE 29

(3R)-3-{[(9-hydroxy-9H-fluoren-9-yl)carbonyl]oxy}-1-methyl-1-(4-oxo-4-phenylbutyl)pyrrolidinium formate 0.575 g (1.858 mmol) of 9-Hydroxy-9H-fluorene-9-carboxylic acid (3R)-1-methylpyrrolidin-3-yl ester (Intermediate I-10) and 1.018 g (5.576 mmol) of 4-chloro-1-phenylbutan-1-one in 6 ml of THF were refluxed for 20 days. After this time THF was poured off, and the residue was washed with THF in order to eliminate the alkylating agent. The product obtained (234 mg) was purified by preparative HPLC-MS to give 65 mg (7%) of the title compound (mixture of two stereoisomers) as a formate.

MS [M−HCOO$^-$]$^+$: 456.

Conditions used in the purification HPLC-MS:
Column: Symmetry C18, 100 A, 5 μm 19×100 mm, Waters.
Mobile phase: A ($H_2O$ 0.1% HCOONH ((*): Configuration not assigned).

Method (c)

Compounds of formula (V) which are methyl esters may be prepared by standard methods of esterification described in the literature from the corresponding carboxilic acid, or following the procedures described in WO 01/04118 A2, or according to procedures described in literature: FR 2012964; Larsson. L et al. Acta Pharm. Suec. (1974), 11(3), 304–308; Nyberg, K. et al. Acta Chem. Scand. (1970), 24, 1590–1596; Cohen, V. I. et al. J. Pharm. Sciences (1992), 81, 326–329; E. Atkinson et al. J. Med. Chem. (1977), 20 (12), 1612–1617.

Intermediate I-1

Preparation of 2-Hydroxy-2,2-dithien-2-ylacetic acid (3R)-1-(2-phenoxyethyl)pyrrolidin-3-yl ester 1.33 g of 2-Hydroxy-2,2-dithien-2-ylacetic acid methyl ester (0.0052 mol) were dissolved in 40 ml of toluene. To this solution were added 1.08 g (0.0052 mol) of (3R)-1-(2-phenoxyethyl)pyrrolidin-3-ol (Intermediate I-15), and 0.104 g (0.0026 mol) of HNa (60% dispersion in mineral oil). The mixture was stirred 30 min at room temperature, refluxed for 45 minutes, and then refluxed with continuous removal of distillate with replacement with fresh toluene when necessary for 1.5 hours. The cooled mixture was extracted with 2N HCl acid, the aqueous layer basified with $K_2CO_3$ and extracted with $CHCl_3$. The organic layer was washed with water, dried over $Na_2SO_4$ and evaporated to yield 1.77 g of an oil which was purified by chromatography on silica gel eluting with chloroform/ethanol/$NH_4OH$ (200:8:1). Appropriate fractions were combined and evaporated to yield 1.22 g of the title product as an oil (54.7%). This product was solidified by formation of the oxalate salt.

2-Hydroxy-2,2-dithien-2-ylacetic acid (3R)-1-(2-phenoxyethyl)pyrrolidin-3-yl ester oxalate salt: 1.03 g (0.0024 mol) of the free base were treated with oxalic acid (0.216 g, 0.0024 mol) in acetone/ether. A white solid was obtained which was filtered and washed with ether. The yield was 0.91 g (73.4%).

m.p.: 134° C.
$^1$H-NMR (DMSO-$d_6$): δ 1.80–1.95 (m, 1H), 2.20–2.35 (m, 1H), 2.90–3.25 (m, 5H), 3.25–3.35 (m, 1H), 4.16 (t, 2H), 5.33 (m, 1H), 6.95–7.0 (m, 5H), 7.10–7.15 (m, 2H), 7.25–7.35 (m, 2H), 7.45–7.50 (m, 2H).
MS [M+1]$^+$: 430

2-Hydroxy-2,2-dithien-2-ylacetic acid methyl ester may be prepared as described in Nyberg, K. et al. Acta Chem. Scand. (1970), 24, 1590–1596.

Intermediate I-2

Preparation of 2-Hydroxy-2,2-dithien-2-ylacetic acid (3R)-1-(3-phenoxypropyl)pyrrolidin-3-yl ester Prepared as described in Intermediate I-1 from 2-Hydroxy-2,2-dithien-2-ylacetc acid methyl ester and (3R)-1-(3-phenoxypropyl)pyrrolidin-3-ol (Intermediate I-16). The yield was 0.85 g (49%) of the title product as an oil. A portion of this product was solidified by formation of the oxalate salt.

2-Hydroxy-2,2-dithien-2-ylacetic acid (3R)-1-(3-phenoxypropyl)pyrrolidin-3-yl ester oxalate salt: 0.3 g (0.000676 mol) of the free base were treated with oxalic acid (0.060 g, 0.00067 mol) in acetone/ether. A solid was obtained which was filtered and washed with ether. The yield was 0.24 g (67%).

m.p.: 115.6–117.2° C.
$^1$H-NMR (DMSO-$d_6$): δ 1.90–2.05 (m, 3H), 2.20–2.40 (m, 1H), 2.90–3.25 (m, 5H), 3.40–3.50 (m, 1H), 4.0 (t, 2H), 5.38 (m, 1H), 6.90–7.0 (m, 5H), 7.10–7.15 (m, 2H), 7.25–7.35 (m, 2H), 7.45–7.50 (m, 2H).
MS [M+1]$^+$: 444

Intermediate I-3

Preparation of 2-Hydroxy-2,2-dithien-2-ylacetic acid (3R)-1-(3-thien-2-ylpropyl)pyrrolidin-3-yl ester Prepared as described in Intermediate I-1 from 2-Hydroxy-2,2-dithien-2-ylacetic acid methyl ester and (3R)-1-(3-thien-2-ylpropyl)pyrrolidin-3-ol (Intermediate I-17). The yield was 0.83 g (49.1%) of the title product as an oil. A portion of this product was solidified by formation of the oxalate salt.

2-Hydroxy-2,2-dithien-2-ylacetic acid (3R)-1-(3-thien-2-ylpropyl)pyrrolidin-3-yl ester oxalate salt: 0.3 g (0.00069 mol) of the free base were treated with oxalic acid (0.062 g, 0.00069 mol) in acetone/ether. A solid was obtained which was filtered and washed with ether. The yield was 0.27 g (75%).

m.p.: 112.6–114.1° C.
$^1$H-NMR (DMSO-$d_6$): δ 1.80–2.05 (m, 3H), 2.20–2.40 (m, 1H), 2.70–3.0 (m, 4H), 3.0–3.30 (m, 3H), 3.40–3.55 (m, 1H), 5.37 (m, 1H), 6.85–7.05 (m, 4H), 7.10–7.20 (m, 2H), 7.30–7.40 (m, 1H), 7.45–7.50 (m, 2H), 8–10 (broad band, 3H).
MS [M+1]$^+$: 434

Intermediate I-4

Preparation of 2-Hydroxy-2,2-dithien-2-ylacetic acid (3R)-1-phenethylpyrrolidin-3-yl ester Prepared as described in Intermediate I-1 from 2-Hydroxy-2,2-dithien-2-ylacetic acid methyl ester and (3R)-1-phenethylpyrrolidin-3-ol (Intermediate I-18). The yield was 0.98 g (50.5%) of the title product.

m.p.: 114.3–115.7° C.
$^1$H-NMR (CDCl$_3$): δ 1.85–1.95 (m, 1H), 2.20–2.35 (m, 1H), 2.50–2.62 (m, 1H), 2.62–2.82 (m, 6H), 2.85–3.0 (m, 1H), 4.92 (broad singlet, 1H, OH), 5.35 (m, 1H), 6.92–7.0 (m, 2H), 7.15–7.35 (m, 9H)
MS [M+1]$^+$: 414

Method (d)
The preparation of the methyl ester derivatives of formula (V) has been described in method (c).

Intermediate I-5
Preparation of 2-hydroxy-2,2-dithien-2-ylacetic acid (3R)-1-methylpyrrolidin-3-yl ester 1 g of 2-Hydroxy-2,2-dithien-2-ylacetic acid methyl ester (0.0039 mol) was dissolved in 30 ml of toluene. To this solution were added 0.394 g (0.0039 mol) of (3R)-1-methylpyrrolidin-3-ol (Intermediate I-19), and 0.078 g (0.00195 mol) of HNa (60% dispersion in mineral oil). The mixture was stirred 30 min at room temperature, refluxed for 1 hour, and then refluxed with continuous removal of distillate with replacement with fresh toluene when necessary for 2 hours. The cooled mixture was extracted with 2N HCl, the aqueous layer was washed with a small volume of ethyl acetate, basified with solid $K_2CO_3$ and extracted three times with ethyl acetate. The organic layer was washed with brine, dried over $Na_2SO_4$ and evaporated. The yield was 0.73 g (58%) of the title product (structure confirmed by $^1$H-NMR). This product was purified by chromatography on silica gel eluting with chloroform/ethanol/$NH_4OH$ (200:8:1). Appropriate fractions were combined and evaporated to give the title compound.

m.p.: 84° C.
$^1$H-NMR (DMSO-$d_6$): δ 1.62–1.75 (m, 1H), 2.10–2.32 (m, 2H), 2.21 (s, 3H), 2.45–2.55 (m, 1H), 2.55–2.70 (m, 2H), 5.18 (m, 1H), 6.95–7.0 (m, 2H), 7.05–7.15 (m, 2H), 7.32 (s, 1H, OH), 7.45–7.50 (m, 2H).
MS [M+1]$^+$: 324

Intermediate I-6

Preparation of 2-Hydroxy-2,2-dithien-2-ylacetic acid (3S)-1-methylpyrrolidin-3-yl ester Prepared as described in Intermediate I-5 from 0.98 g (0.00385 mol) of 2-Hydroxy-2,2-dithien-2-ylacetic acid methyl ester in 30 ml of toluene, 0.39 g (0.00385 mol) of (3S)-1-methylpyrrolidin-3-ol (Intermediate I-20) and 0.108 g (0.0027 mol) of HNa (60% dispersion in mineral oil). The yield was 0.31 g (25%) of the title product.

m.p.: 84° C.
$^1$H-NMR (DMSO-d$_6$): δ (Equivalent to I-5)
MS [M+1]$^+$: 324

Intermediate I-7

Preparation of 2-hydroxy-2,2-dithien-2-ylacetic acid 1-methylpyrrolidin-3-yl ester Prepared as described in Intermediate I-5 from 2-Hydroxy-2,2-dithien-2-ylacetic add methyl ester and 1-methylpyrrolidin-3-ol (commercially available). The yield was 0.96 g (30%).

$^1$H-NMR (DMSO-d$_6$): δ (Equivalent to I-5)
MS [M+1]$^+$: 324

Intermediate I-8

Preparation of 9H-Xanthene-9-carboxylic acid (3R)-1-methylpyrrolidin-3-yl ester 2 g of 9H-Xanthene-9-carboxylic acid (0.0088 mol) were dissolved in 30 ml of CHCl$_3$ (ethanol free). The solution was cooled at 0° C. and 1.08 ml (0.0123 mol) of oxalyl chloride and a drop of DMF was added. The mixture was stirred and allowed to warm to room temperature. After an hour at this temperature the solvents were evaporated and the residue was dissolved in CHCl$_3$ and evaporated again. This procedure was repeated two times. The solid obtained (2.19 g) was dissolved in 20 ml of CHCl$_3$ and added to a solution of 0.975 g (0.0097 mol) of (3R)-1-methylpyrrolidin-3-ol (Intermediate I-19) in 15 ml of CHCl$_3$ cooled at 0–5° C. The reaction mixture was allowed to warm to room temperature and stirred overnight. The solvent was evaporated and the residue was dissolved in toluene and extracted with HCl 2N. The aqueous layer was basified with K$_2$CO$_3$ and extracted with CHCl$_3$. The organic layer was washed with brine, dried over Na$_2$SO$_4$ and evaporated to dryness to yield 2.53 g (93%) of the title product as an oil.

$^1$H-NMR (CDCl$_3$): δ 1.65–1.85 (m, 1H), 2.05–2.42 (m, 2H), 2.30 (s, 3H), 2.45–2.60 (m, 1H), 2.60–2.80 (m, 2H), 5.0 (s, 1H), 5.05–5.20 (m, 1H), 7.0–7.25 (m, 4H), 7.25–7.40(m, 4H).

MS [M+1]$^+$: 310

This product was solidified by formation of the oxalate salt.

9H-Xanthene-9-carboxylic acid (3R)-1-methylpyrrolidin-3-yl ester oxalate salt: 2.53 g (0.0082 mol) of the free base were treated with oxalic acid (0.74 g, 0.0082 mol) in acetone/ether. A solid was obtained which was filtered and washed with ether. The yield was 2.48 g (75.8%).

m.p.: 155.0–155.8° C.
MS [M+1]$^+$: 310

Intermediate I-9

Preparation of 9H-Xanthene-9-carboxylic acid (3S)-1-methylpyrrolidin-3-yl ester

This compound was prepared as described in Intermediate I-8 starting from 9H-Xanthene-9-carboxylic and (3S)-1-methylpyrrolidin-3-ol (Intermediate I-20).

9H-Xanthene-9-carboxylic acid (3S)-1-methylpyrrolidin-3-yl ester oxalate salt was prepared as is described for the oxalate salt of Intermediate I-8.

9H-Xanthene-9-carboxylic acid 1-methylpyrrolidin-3-yl ester (sulphate salt) is described in B. V. Franko et al., J. Med. Pharm. Chem., (1960), 2 (5), 523–540.

Intermediate I-10

Preparation of 9-Hydroxy-9H-fluorene-9-carboxylic acid (3R)-1-methylpyrrolidin-3-yl ester 0.980 g (0.0041 mol) of 9-Hydroxy-9H-fluorene-9-carboxylic acid methyl ester were dissolved in 30 ml of toluene. To this solution 0.412 g (0.0041 mol) of (3R)-1-methylpyrrolidin-3-ol (Intermediate I-19) and a catalitic amount of Na$^{(0)}$ were added and the mixture was refluxed using a Dean-Stark system for 24 hours. The reaction mixture was cooled, and extracted with HCl 2N. The aqueous layer was basified with K$_2$CO$_3$ and extracted with AcOEt (3×100 ml). The organic layers were combined, dried over Na$_2$SO$_4$ and evaporated to dryness to yield a residue which was purified by chromatography on silica gel eluting with chloroform plus isopropanol (0%→20%). Appropiate fractions were combined and evaporated to give 0.390 g (31%) of the title compound as an oil.

$^1$H-NMR (CDCl$_3$): δ 7.65 (d, 2H), 7.51 (d, 2H), 7.43–7.37 (m, 2H), 7.33–7.27 (m, 2H), 5.11 (m, 1H), 2.65–2.59 (m, 1H), 2.26–2.17 (m, 3H), 2.07–1.93 (m, 1H), 1.99 (s, 3H), 1.57–1.45 (m, 1H).

MS [M+1]$^+$: 310

9-Hydroxy-9H-fluorene-9-carboxylic acid methyl ester was prepared from 9-Hydroxy-9H-fluorene-9-carboxylic acid by a standard method of esterification.

Intermediate I-11

Preparation of 2-Cyclohexyl-2-fur-2-yl-2-hydroxyacetic acid (3R)-1-methylpyrrolidin-3-yl ester 5.0 g (0.021 mol) of 2-Cyclohexyl-2-fur-2-yl-2-hydroxyacetic acid methyl ester were dissolved in 150 ml of dry toluene. To this solution 2.12 g (0.021 mol) of (3R)-1-methylpyrrolidin-3-ol (Intermediate I-19) and 500 mg (0.021 mol) of HNa were added and the mixture was refluxed using a Dean-Stark system for 24 hours. The reaction mixture was cooled, and extracted with HCl 2N. The aqueous layer was basified with K$_2$CO$_3$ and extracted with AcOEt (3×100 ml). The organic layers were combined, dried over Na$_2$SO$_4$ and evaporated to dryness to yield a residue which was purified by chromatography on silica gel eluting with chloroform plus isopropanol (0%→10%). Appropriate fractions were combined and evaporated to give 1.37 g (21%) of the title product as an oil.

$^1$H-NMR (CDCl$_3$): δ 7.38 (s, 1H), 6.37–6.30 (m, 2H), 5.30–5.22 (m, 1H), 2.87–2.58 (m, 3H), 2.50–2.10 (m, 3H), 2.36 and 2.32 (s, 3H), 1.93–1.62 (m, 4H), 1.38–1.07 (m, 7H).

MS [M+1]$^+$: 308

2-Cyclohexyl-2-fur-2-yl-2-hydroxyacetic acid methyl ester can be prepared according to methods described in WO 01/04118 A2

Intermediate I-12

Preparation of 2-Cyclohexyl-2-fur-2-yl-2-hydroxyacetic acid 1-ethylpyrrolidin-3-yl ester 1 g (0.0042 mol) of 2-Cyclohexyl-2-fur-2-yl-2-hydroxyacetic acid methyl ester was dissolved in 12 ml of EtOH and 6 ml of a solution of NaOH 2N were added. This mixture was stirred at 600 for 1 hour. After this time, the EtOH was evaporated and the residue was acidified with HCl 10%. The aqueous solution was extracted with AcOEt (2×100 ml). The organic layers were combined, dried and evaporated to obtain a residue (2-cyclohexyl-2-fur-2-yl-2-hydroxyacetic acid) which was used without further purification. The acid obtained was dissolved in dry DMF (12 ml) and 0.817 g (0.005 mol) of 1,1'-carbonildimidazol were added. The mixture was stirred for 1 h at room temperature. After this time the sodium salt of 1-ethylpyrrolidin-3-ol (prepared by addition of HNa (0.1 g, 0.0046 mol) to a solution of 1-ethylpyrrolidin-3-ol (0.5319, 0.0046 mol) in 5 ml of dry DMF) was added. After stirring 15 h at room temperature the reaction mixture was treated with water, and the aqueous phase was extracted with $Et_2O$ (2×100 ml). The organic phases were combined, washed with water and dried. After removal of the solvent the product obtained was purified by chromatography on silica gel eluting with chloroform plus isopropanol (5%→15%). The yield was 460 mg (34% related to starting methyl ester) of the title product.

$^1$H-NMR (CDCl$_3$): δ 1.05–1.45 (m, 10H), 1.60–2.10 (m, 4H), 2.10–2.35 (m, 2H), 2.40–2.75 (m, 5H), 2.85–3.0 (m, 1H), 3.76 (bs, OH, 1H), 5.27 (m, 1H), 6.30–6.40 (m, 2H), 7.39 (s, 1H).

MS [M+1]$^+$: 322

2-Cyclohexyl-2-fur-2-yl-2-hydroxyacetic acid methyl ester can be prepared according to methods described in WO 01/04118 A2

1-ethylpyrrolidin-3-ol is commercially available.

Intermediate I-13

(2R)-2-Cyclopentyl-2-hydroxy-2-phenylacetic acid (3R)-1-methylpyrrolidin-3-yl ester 0.545 g (0.0025 mol) of (2R)-2-cyclopentyl-2-hydroxy-2-phenylacetic acid were dissolved in 8 ml of dry DMF. To this solution 0.481 g (0.003 mol) of 1,1'-carbonildiimidazol were added and the mixture was stirred at room temperature for 1 h. After this time, the mixture obtained was added to a suspension of (3R)-1-methylpyrrolidin-3-ol (Intermediate I-19, 0.531 g, 0.0046 mol) and HNa (0.065 g, 0.0027 mol) in 3 ml of dry DMF. After stirring 26 h at room temperature the reaction mixture was treated with water and extracted two times with Et$_2$O. The organic layers were combined, washed with water and dried. The residue was purified by silica gel column chromatography (eluent: CHCl$_3$ plus isopropanol 0%→10%) to obtain 450 mg (60%) of the title product as an oil.

$^1$H-NMR (CDCl$_3$): δ 7.60–7.56 (m, 2H), 7.29–7.15 (m, 3H), 5.19–5.11 (m, 1H), 3.77 (bs, OH, 1H), 2.92–2.79 (m, 1H), 2.79–2.16 (m, 5H), 2.26 (s, 3H), 1.85–1.72 (m, 1H), 1.61–1.18 (m, 8H).

MS [M+1]$^+$: 304

(2R)-2-Cyclopentyl-2-hydroxy-2-phenylacetic acid is described in M. Mitsuya et al.: Bioorg. Med. Chem., (1999), 7, 2555–2567.

Intermediate I-14

(2R)-2-Cyclopentyl-2-hydroxy-2-phenylacetic acid 1-ethylpyrrolidin-3-yl ester 0.655 g (0.00297 mol) of (2R)-2-Cyclopentyl-2-hydroxy-2-phenylacetic acid were dissolved in 8 ml of dry DMF. To this solution 0.580 g (0.0036 mol) of 1,1'-carbonildiimidazol were added and the mixture was stirred at room temperature for 1 h. After this time, the mixture obtained was added to a suspension (cooled at 0° C.) of 1-ethylpyrrolidin-3-ol (0.390 ml g, 0.0033 mol) and HNa (0.078 g, 0.0033 mol) in 4 ml of dry DMF. After stirring 15 h at room temperature the reaction mixture was treated with water and extracted three times with Et$_2$O. The organic layers were combined, washed with water and dried. The residue was purified by silica gel column chromatography (eluent: CHCl$_3$ plus isopropanol 0%→5%) to obtain 610 mg (65%) of the title product as an oil.

$^1$H-NMR (CDCl$_3$): δ 1.05–1.15 (m, 3H), 1.25–1.95 (m, 10H), 2.10–2.35 (m, 1H), 2.40–3.0 (m, 6H), 3.79 (bs, 1H, OH), 5.23 (m, 1H), 7.24–7.36 (m, 3H), 7.65–7.67 (m, 2H).

MS [M+1]$^+$: 318

(2R)-2-Cyclopentyl-2-hydroxy-2-phenylacetic acid is described in M. Mitsuya et al.; Bioorg. Med. Chem., (1999), 7, 2555–2567.

1-ethylpyrrolidin-3-ol is commercially available.

Method (e)

Intermediate I-15

Preparation of (3R)-1-(2-phenoxyethyl)pyrrolidin-3-ol 0.5 g (0.0057 mol) of (3R)-pyrrolidin-3-ol (commercially available) were dissolved in 15 ml of acetonitrile. To this solution were added 1.32 g (0.0065 mol) of (2-bromoethoxy)benzene, 0.095 g (0.00057 mol) of KI and 1.57 g (0.0114 mol) of K$_2$CO$_3$. This mixture was stirred during 72 h at room temperature. The solid was filtered and the solvent was evaporated to dryness. CHCl$_3$ was added to the residue and the solution obtained was washed with water and brine, dried over Na$_2$SO$_4$ and the solvent was evaporated to obtain 1.43 g of an oil. This product was purified by chromatography on silica gel eluting with chloroform/methanol/NH$_4$OH (90:10:1). The yield was 1.08 g of the title compound (91.5%).

MS [M+1]$^+$: 208

$^1$H-NMR (CDCl$_3$): δ 1.80 (m, 1H), 2.20 (m, 1H), 2.40 (m, 1H), 2.65 (m, 1H), 2.75–3.10 (m, 4H), 4.10 (t, 2H), 4.35 (m, 1H), 6.95 (m, 3H), 7.30 (m, 2H).

(3R)-1-(2-phenoxyethyl)pyrrolidin-3-ol is described in WO 9625417 A1.

Intermediate I-16

Preparation of (3R)-1-(3-phenoxypropyl)pyrrolidin-3-ol

Prepared as in Intermediate I-15 from (3R)pyrrolidin-3-ol (commercially available) and (3-bromopropoxy)benzene. The yield was 2.26 g (71.3%) of the title compound.

MS [M+1]$^+$: 222

$^1$H-NMR (CDCl$_3$): δ 1.75 (m, 1H), 2.0 (m, 2H), 2.10–2.40 (m, 2H), 2.50 (m, 1H), 2.60–2.80 (m, 3H), 2.90 (m, 1H), 4.0 (t, 2H), 4.35 (m, 1H), 6.90 (m, 3H), 7.30 (m, 2H).

Intermediate I-17

Preparation of (3R)-1-(3-thien-2-ylpropyl)pyrrolidin-3-ol

Prepared as in Intermediate I-15 from (3R)pyrrolidin-3-ol (commercially available) and 2-(3-bromopropyl)thiophene. The yield was 1.02 g (85%) of the title compound.

MS [M+1]$^+$: 212

$^1$H-NMR (CDCl$_3$): δ 1.65–2.0 (m, 3H), 2.10–2.35 (m, 2H), 2.40–2.60 (m, 3H) 2.70 (m, 1H), 2.80–3.0 (m, 3H), 4.35 (m, 1H), 6.80 (m, 1H), 6.90 (m, 1H), 7.10 (m, 1H).

Intermediate I-18

Preparation of (3R)-1-phenethylpyrrolidin-3-ol

Prepared as in Intermediate I-15 from (3R)pyrrolidin-3-ol (commercially available) and (2-bromoethyl)benzene. The yield was 0.91 g (83.5%) of the title compound.
MS [M+1]$^+$: 192
$^1$H-NMR (CDCl$_3$): δ 1.65–1.85 (m, 1H), 2.10–2.40 (m, 2H), 2.55 (m, 1H), 2.65–2.90 (m, 5H), 2.90–3.05 (m, 1H), 4.35 (m, 1H), 7.10–7.40 (m, 5H).

1-phenethylpyrrolidin-3-ol is described in Zhu, Y-Q. et al, Yao Hsuch Hsuch Pao (1981), 16(3), 199–210.

Method (f)

Intermediate I-19

Preparation of (3R)-1-methylpyrrolidin-3-ol 15 g (0.172 mol) of (3R)-pyrrolidin-3-ol (commercially available) were dissolved in 240 ml of MeOH. This solution was cooled to 10–15° C., and formaldehyde (124.5 ml of a 36% solution in water, diluted with 125 ml of MeOH) and NaBH$_4$ (16.27 g, 0.43 mol) were added in small portions, alternatively during 1 h, maintaining the temperature at 10–15° C. After 20 min the mixture was warmed to room temperature and the reaction continued for 1 hour. The reaction mixture was acidified with HCl 2N, stirred during 20 minutes and neutralized with solid NaHCO$_3$. MeOH and most of the water were evaporated and the residue was diluted with a small quantity of water, basified with solid K$_2$CO$_3$ and exhaustively extracted with CHCl$_3$. The organic phases were combined and dried over Na$_2$SO$_4$. CHCl$_3$ was evaporated to give an oil which was purified by Kugelrohr distillation at reduced pressure (0.2–0.3 mbar, 50–60° C. oven) to give 14.91 g (85.6%) of the title product.
$^1$H-NMR (CDCl$_3$): δ 1.60–1.80 (m, 1H), 2.10–2.40 (m, 5H), 2.40–2.70 (m, 2H), 2.75–2.95 (m, 1H), 4.20–4.40 (m, 1H), 4.40–4.50 (bs, 1H, OH).

A sample of 1 g of this material was treated with 1.5 g of (2R,3R)-tartaric acid in MeOH/ether to obtain 2.3 g of the tartrate salt [α]$_D$=+10.60 (c=1, H$_2$O)$^1$.
$^1$ [α]$^{22}_D$=+11.1° (c=9.57, H$_2$O), Sleevi et al. J. Med. Chem., (1991), Vol 34, n° 4, 1314–1328).

Intermediate I-20

Preparation of (3S)-1-methylpyrrolidin-3-ol

Prepared as in Intermediate I-19 from 2 g of (3S)-pyrrolidin-3-ol (commercially available). The yield was 1.65 g (71.1%) of a pale yellow oil which was not necessary to purify by distillation.
This material was treated with 2.5 g of (2S,3S)-tartaric acid in MeOH/ether to obtain 3.65 g of the tartrate salt [α]$_D$=−11.3° (c=1, H$_2$O)$^2$.
$^2$[α]$^{22}_D$=−11.5° (c=1, H$_2$O), Sleevi et al. J. Med. Chem., (1991), Vol 34, n° 4, 1314–1328).

Also included within the scope of the present invention are pharmaceutical compositions which comprise, as the active ingredient, at least one pyrrolidinium derivative of formula (I) in association with a pharmaceutically acceptable carrier or diluent. Preferably the composition is made up in a form suitable for oral administration.

The pharmaceutically acceptable carrier or diluents which are mixed with the active compound or compounds, to form the composition of this invention are well-known per se and the actual excipients used depend inter alia on the intended method of administration of the composition.

Compositions of this invention are preferably adapted for oral administration. In this case, the composition for oral administration may take the form of tablets, film-coated tablets, liquid inhalant, powder inhalant and inhalation aerosol; all containing one or more compounds of the invention; such preparations may be made by methods well-known in the art.

The diluents which may be used in the preparations of the compositions include those liquid and solid diluents which are compatible with the active ingredient, together with coloring or flavouring agents, if desired. Tablets or film-coated tablets may conveniently contain between 1 and 500 mg, preferably from 5 to 300 mg of active ingredient. The inhalant compositions may contain between 1 μg and 1,000 μg, preferably from 10 μg to 800 μg of active ingredient. In human therapy, the dose of the compound of formula (I) depend on the desired effect and duration of treatment; adult doses are generally between 3 mg and 300 mg per day as tablets and 10 μg and 800 μg per day as inhalant composition.

Pharmacological Action

The results on human muscarinic receptors binding and in the test on bronchospasm in guinea pig, were obtained as described below.

Human Muscarinic Receptor Studies.

The binding of [3H]-NMS to human muscarinic receptors was performed according to Waelbroeck et al (1990), Mol. Pharmacol., 38: 267–273. Assays were carried out at 25° C. Membrane preparations from stably transfected chinese hamster ovary-K1 cells (CHO) expressing the genes for the human M3 muscarinic receptors were used.

For determination of IC$_{50}$, membrane preparations were suspended in DPBS to a final concentration of 89 μg/ml for the M3 subtype. The membrane suspension was incubated with the tritiated compound for 60 min. After incubation the membrane fraction was separated by filtration and the bound radioactivity determined. Non-specific binding was determined by addition of 10$^{-4}$ M atropine. At least six concentrations were assayed in duplicate to generate individual displacement curves.

Our results show that the compounds of the present invention have high affinities for M3 muscarinic receptors, preferably human muscarinic receptors. Thus, the IC$_{50}$ of the preferred compounds of the invention is lower than 35 nM. Most preferred compounds, such as the compounds of examples 1 to 8 described below, have an IC$_{50}$ lower than 20 nM.

Test on Bronchospasm in Guinea Pig

The studies were performed according to H. Konzett and F. Rössler (1940), Arch. Exp. Path. Pharmacol. 195: 71–74. Aqueous solutions of the agents to be tested were nebulized and inhaled by anaesthetized ventilated male guinea pigs (Dunkin-Hartley). Bronchial response to intravenous acetylcholine challenge was determined before and after drug administration and the changes in pulmonary resistance at several time-points were expressed as percent of inhibition of bronchospasm.

The compounds of the present invention inhibited the bronchospasm response to acetylcholine with high potency and a long duration of action.

From the above described results one of ordinary skill in the art can readily understand that the compounds of the present invention have excellent M3 antimuscarinic activity and thus are useful for the treatment of diseases in which the M3 muscarinic receptor is implicated, including respiratory disorders such as chronic obstructive pulmonary disease (COPD), bronchitis, bronchial hyperreactivity, asthma, cough and rhinitis; urological disorders such as urinary incontinence, pollakiuria, neurogenic or unstable bladder, cystospasm and chronic cystitis; gastrointestinal disorders such as irritable bowel syndrome, spastic colitis, diverticulitis and peptic ulceration; and cardiovascular disorders such as vagally induced sinus bradycardia.

The present invention further provides a compound of formula (I) or a pharmaceutically acceptable composition comprising a compound of formula (I) for use in a method of treatment of the human or animal body by therapy, in particular for the treatment of respiratory, urological or gastrointestinal disease or disorder.

The present invention further provides the use of a compound of formula (I) or a pharmaceutically acceptable composition comprising a compound of formula (I) for the manufacture of a medicament for the treatment of a respiratory, urological or gastrointestinal disease or disorder.

Further, the compounds of formula (I) and pharmaceutical compositions comprising a compound of formula (I) can be used in a method of treating a respiratory, urological or gastrointestinal disease or disorder, which method comprises administering to a human or animal patient in need of such treatment an effective, non-toxic, amount of a compound of formula (I) or a pharmaceutical composition comprising a compound of formula (I).

Further, the compounds of formula (I) and pharmaceutical compositions comprising a compound of formula (I) can be used in combination with other drugs effective in the treatment of these diseases. For example with $\beta_2$ agonists, steroids, antiallergic drugs, phosphodiesterase IV inhibitors and/or leukotriene D4 (LTD4) inhibitors, for simultaneous, separate or sequential use in the treatment of a respiratory disease.

The present invention will be further illustrated by the following examples. The examples are given by way of illustration only and are not to be construed as a limiting.

EXAMPLE 1

3-(2-Hydroxy-2,2-dithien-2-ylacetoxy)-1-methyl-1-phenethylpyrrolidinium trifluoroacetate The title compound was obtained as a mixture of four stereoisomers according to method (b) from Intermediate I-7.

The yield of the final step was 90 mg (30%).
MS [M−CF3COO]$^+$: 428

EXAMPLE 2

(3R)-3-(2-Hydroxy-2,2-dithien-2-ylacetoxy)-1-methyl-1-phenethylpyrrolidinium bromide The title compound was obtained as a mixture of two stereoisomers according to method (a) from Intermediate I-4. The yield of the final step was 0.31 g (84.7%).
m.p.: 143.7–158.6° C.
HPLC: mixture of diastereomers 44:56.
$^1$H-NMR (DMSO-d$_6$): δ 2.10–2.30 (m, 1H), 2.65–2.85 (m, 1H), 3.02–3.15 (m, 2H), 3.05 and 3.23 (s, 3H), 3.40–3.85 (m, 5H), 3.90–4.05 (m, 1H), 5.57 (m, 1H), 6.90–6.95 (m, 1H), 7.0–7.05 (m, 1H), 7.05–7.22 (m, 2H), 7.25–7.42 (m, 5H), 7.42–7.60 (m, 3H)
MS [M−Br]$^+$: 428

EXAMPLE 3

(3R)-3-(2-Hydroxy-2,2-dithien-2-ylacetoxy)-1-methyl-1-(2-phenoxyethyl)pyrrolidinium bromide The title compound was obtained as a mixture of two stereoisomers according to method (a) from Intermediate I-1. The yield of the final step was 0.47 g (81.6%).
m.p.: 54.9–65.3° C.
$^1$H-NMR: mixture of diastereomers 50:50.
$^1$H-NMR (DMSO-d$_6$): δ 2.10–2.25 (m, 1H), 2.70–2.82 (m, 1H), 3.05 and 3.21 (s, 3H), 3.64–4.10 (m, 6H), 4.40 and 4.46 (m, 2H), 5.56 (m, 1H), 6.97–7.04 (m, 5H), 7.13–7.17 (m, 2H), 7.33–7.39 (m, 2H), 7.48–7.54 (m, 3H)
MS [M−Br]$^+$: 444

EXAMPLE 4

Described in Method (b)

(1*,3R)-3-(2-Hydroxy-2,2-dithien-2-ylacetoxy)-1-methyl-1-(2-phenoxyethyl)pyrrolidinium bromide (diastereomer 1)

The title compound was obtained as a single isomer according to method (b) from Intermediate I-5.
The yield of the final step was 0.85 g (52.5% based on single isomer).
m.p.: 198.8–199.4° C.
$^1$H-NMR: diastereomer 1, 95:5
$^1$H-NMR (DMSO-d$_6$): δ 2.10–2.25 (m, 1H), 2.65–2.82 (m, 1H), 3.20 (s, 3H), 3.60–3.90 (m, 5H), 3.95–4.05 (m, 1H), 4.38 (m, 2H), 5.56 (m, 1H), 6.95–7.05 (m, 5H), 7.10–7.20 (m, 2H), 7.30–7.42 (m, 2H), 7.45–7.60 (m, 3H).
MS [M−Br]$^+$: 444

(* Configuration not assigned)

EXAMPLE 5

Described in Method (b)

(1*,3R)-3-(2-Hydroxy-2,2-dithien-2-ylacetoxy)-1-methyl-1-(2-phenoxyethyl)pyrrolidinium bromide (diastereomer 2)

The title compound was obtained as a single isomer according to method (b) from Intermediate I-5.
The yield of the final step was 0.47 g (29% based on single isomer).
m.p.: 85.9–87.6° C.
$^1$H-NMR: diastereomer 2, 95:5
$^1$H-NMR (DMSO-d$_6$): δ 2.10–2.25 (m, 1H), 2.65–2.85 (m, 1H), 3.04 (s, 3H), 3.62–3.72 (m, 1H), 3.78–3.90 (m, 4H), 3.97–4.04 (m, 1H), 4.45 (m, 2H), 5.55 (m, 1H), 6.98–7.03 (m, 5H), 7.12–7.16 (m, 2H), 7.32–7.37 (m, 2H), 7.50–7.52 (m, 3H).
MS [M−Br]$^+$: 444

(* Configuration not assigned)

EXAMPLE 6

Described in Method (a)

(3R)-3-(2-Hydroxy-2,2-dithien-2-ylacetoxy)-1-methyl-1-(3-thien-2-ylpropyl)pyrrolidinium bromide The title compound was obtained as a mixture of two stereoisomers according to method (a) from Intermediate I-3. The yield of the final step was 0.34 g (93.2%).

$^1$H-NMR: mixture of diastereomers 55:45

$^1$H-NMR (DMSO-$d_6$): δ 1.95–2.20 (m, 3H), 2.60–2.80 (m, 2H), 2.80–2.90 (m, 1H), 2.94 and 3.10 (s, 3H), 3.20–3.45 (m, 2H), 3.45–3.95 (m, 4H), 5.52 (m, 1H), 6.90–7.05 (m, 4H), 7.10–7.20 (m, 2H), 7.37 (m, 1H), 7.40–7.55 (m, 3H).

MS [M−Br]$^+$: 448

EXAMPLE 7

Described in Method (b)

3-(2-Hydroxy-2,2-dithien-2-ylacetoxy)-1-methyl-1-(3-phenoxypropyl) pyrrolidinium bromide The title compound was obtained as a mixture of four stereoisomers according to method (b) from Intermediate I-7. The yield of the final step was 0.75 g (69.4%).

m.p.: 55.3–56.8° C.

$^1$H-NMR, mixture of diastereomers 56:44

$^1$H-NMR (DMSO-$d_6$): δ 2.05–2.30 (m, 3H), 2.60–2.80 (m, 1H), 2.96 and 3.12 (s, 3H), 3.40–3.50 (m, 1H), 3.50–3.82 (m, 4H), 3.85–4.0 (m, 2H), 4.04.10 (m, 1H), 5.52 (m, 1H), 6.90–7.01 (m, 5H), 7.10–7.15 (m, 2H), 7.25–7.35 (m, 2H), 7.42–7.52 (m, 3H)

MS [M−Br]$^+$: 458

EXAMPLE 8

(3R)-3-(2-Hydroxy-2,2-dithien-2-ylacetoxy)-1-methyl-1-(3-phenoxypropyl)pyrrolidinium bromide The title compound was obtained as a mixture of two stereoisomers according to method (a) from Intermediate I-2. The yield of the final step was 0.21 g (70%).

HPLC: mixture of diastereomers 59:41

$^1$H-NMR (DMSO-$d_8$): δ 2.05–2.30 (m, 3H), 2.65–2.80 (m, 1H), 3.0 and 3.15 (s, 3H), 3.40–3.50 (m, 1H), 3.50–3.85 (m, 4H), 3.85–4.0 (m, 2H), 4.04.10 (m, 1H), 5.55 (m, 1H), 6.90–7.05 (m, 5H), 7.10–7.20 (m, 2H), 7.25–7.35 (m, 2H), 7.45–7.55 (m, 3H).

MS [M−Br]$^+$: 458

EXAMPLE 9

Described in Method (a)

(1*,3R)-3-(2-Hydroxy-2,2-dithien-2-ylacetoxy)-1-methyl-1-(3-phenoxypropyl)pyrrolidinium bromide (diastereomer 1)

The title compound was obtained as a single isomer according to method (a) from Intermediate I-2.

The yield of the final step was 0.628 g (80.1% based on single isomer).

m.p.: 86.2–89.6° C.

$^1$H-NMR: diastereomer 1 (diastereomer 2 not observed)

$^1$H-NMR (DMSO-$d_6$): δ 2.10–2.30 (m, 3H), 2.65–2.80 (m, 1H), 3.0 (s, 3H), 3.50–3.65 (m, 3H), 3.70–3.85 (m, 2H), 3.85–3.95 (m, 1H), 4.05 (m, 2H), 5.54 (m, 1H), 6.90–7.05 (m, 5H), 7.10–7.20 (m, 2H), 7.25–7.35 (m, 2H), 7.50–7.55 (m, 3H).

MS [M−Br]$^+$: 458

(* Configuration not assigned)

EXAMPLE 10

Described in Method (a)

(1*,3R)-3-(2-Hydroxy-2,2-dithien-2-ylacetoxy)-1-methyl-1-(3-phenoxypropyl)pyrrolidinium bromide (diastereomer 2)

The title compound was obtained as a single isomer according to method (a) from Intermediate I-2.

The yield of the final step was 0.559 g (71.3% based on single isomer).

m.p.: 87.1–89.0° C.

$^1$H-NMR: diastereomer 2 (diastereomer 1 not observed)

$^1$H-NMR (DMSO-$d_6$): δ 2.05–2.30 (m, 3H), 2.65–2.80 (m, 1H), 3.15 (s, 3H), 3.40–3.55 (m, 2H), 3.55–3.80 (m, 3H), 3.95 (m, 3H), 5.55 (m, 1H), 6.90–7.05 (m, 5H), 7.05–7.20 (m, 2H), 7.30–7.40 (m, 2H), 7.45–7.50 (m, 3H).

MS [M−Br]$^+$: 458

(* Configuration not assigned)

EXAMPLE 11

Described in Method (b)

(1*,3R)-1-Methyl-1-phenethyl-3-(9H-xanthen-9-ylcarbonyloxy)pyrrolidinium bromide (diastereomer 1)

The title compound was obtained as a single isomer according to method (b) from Intermediate I-8.

The yield of the final step was 0.301 g (53.7% based on single isomer).

mp: 232.3–233.1° C.

HPLC: diastereomer 1, 92.5:7.5

$^1$H-NMR (DMSO-$d_6$): δ 2.0–2.15 (m, 1H), 2.55–2.70 (m, 1H), 3.0 (s, 3H), 3.0–3.10 (m, 2H), 3.45–3.75 (m, 5H), 3.85–3.92 (m, 1H), 5.30 (s, 1H), 5.36 (m, 1H), 7.10–7.50 (m, 13H).

MS [M−Br]$^+$: 414

(* Configuration not assigned)

EXAMPLE 12

Described in Method (b)

(1*,3R)-1-Methyl-1-phenethyl-3-(9H-xanthen-9-ylcarbonyloxy)pyrrolidinium bromide (diastereomer 2)

The title compound was obtained as a single isomer according to method (b) from Intermediate I-8.

The yield of the final step was 0.193 g (34.5% based on single isomer).

mp: 79.6–81.2° C.

HPLC: diastereomer 2, 98.8:1.2

¹H-NMR (DMSO-d₆): δ 2.0–2.10 (m, 1H), 2.55–2.70 (m, 1H), 3.0–3.10 (m, 2H), 3.17 (s, 3H), 3.45–3.55 (m, 2H), 3.55–3.75 (m, 3H), 3.85–3.92 (m, 1H), 5.24 (s, 1H), 5.38 (m, 1H), 7.0–7.15 (m, 4H), 7.25–7.50 (m, 9H).
MS [M−Br]⁺: 414

(* Configuration not assigned)

EXAMPLE 13

(1*,3R)-3-(2-Hydroxy-2,2-dithien-2-ylacetoxy)-1-methyl-1-(3-phenylallyl)pyrrolidinium bromide (diastereomer 1)

The title compound was obtained as a single isomer according to method (b) from Intermediate I-5.
The reaction time for the final step (conditions: THF, reflux temperature) was 2 h. Purification by column chromatography (silica gel, eluent: $CH_2Cl_2$ plus isopropanol 30%→80%) gave 358 mg (44.2%) of the title compound (first eluted diastereomer).
¹H-NMR: diastereomer 1 (diastereomer 2 not observed)
¹H-NMR (DMSO-d₆): δ 7.60–7.50 (m, 5H), 7.44–7.34 (m, 3H), 7.16–7.12 (m, 2H), 7.02–6.98 (m, 2H), 6.91 (d, 1H), 6.57–6.45 (m, 1H), 5.55 (m, 1H), 4.24 (d, 2H), 4.04–3.96 (m, 1H), 3.74–3.64 (m, 3H), 2.97 (s, 3H), 2.79–2.67 (m, 1H), 2.23–2.12 (m, 1H).
MS [M−Br]⁺: 440

(* Configuration not assigned)

EXAMPLE 14

(1*,3R)-3-(2-Hydroxy-2,2-dithien-2-ylacetoxy)-1]-methyl-1-(3-phenylallyl)pyrrolidinium bromide (diastereomer 2)

The title compound was obtained as a single isomer according to method (b) from Intermediate I-5.
The reaction time for the final step (conditions: THF, reflux temperature) was 2 h. Purification by column chromatography (silica gel, eluent: $CH_2Cl_2$ plus isopropanol 30%→80%) gave 160 mg (19.8%) of the title compound (second eluted diastereomer).
¹H-NMR: diastereomer 2 (diastereomer 1 not observed)
¹H-NMR (DMSO-d₆): δ 7.58–7.49 (m, 5H), 7.45–7.36 (m, 3H), 7.18 (dd, 1H), 7.13 (dd, 1H), 7.02–6.97 (m, 2H), 6.80 (d, 1H), 6.51–6.39 (m, 1H), 5.56 (m, 1H), 4.05 (d, 2H), 3.93–3.72 (m, 3H), 3.64–3.53 (m, 1H), 3.13 (s, 3H), 2.80–2.71 (m, 1H), 2.24–2.13 (m, 1H).
MS [M−Br]⁺: 440

(* Configuration not assigned)

EXAMPLE 15

(3R)-3-(2-Hydroxy-2,2-dithien-2-ylacetoxy)-1-methyl-1-(4-oxo thien-2-ylbutyl)pyrrolidinium chloride The title compound was obtained as a mixture of two stereoisomers according to method (b) from Intermediate I-5.
The reaction time for the final step (conditions: THF, reflux temperature) was 7 days. Purification of the product by several washings with THF at reflux temperature, gave 120 mg (8%) of the title compound (mixture of two stereoisomers).
HPLC: mixture of diastereomers 38:62

¹H-NMR (DMSO-d₆): δ 8.06–7.98 (m, 2H), 7.60 (s, OH, 1H), 7.52–7.45 (m, 2H), 7.30–7.25 (m, 1H), 7.18–7.11 (m, 2H), 7.02–6.95 (m, 2H), 5.51 (m, 1H), 4.02–3.00 (m, 8H), 3.15 and 3.00 (s, 3H), 2.78–2.65 (m, 1H), 2.23–1.96 (m, 3H).
MS [M−Cl]⁺: 476.

EXAMPLE 16

(1*,3R)-1-[4–4-Fluorophenyl)-4-oxobutyl]-3-(2-hydroxy-2,2-dithien-2-ylacetoxy)-1-methylpyrrolidinium chloride (diastereomer 1)

The title compound was obtained as a single isomer according to method (b) from Intermediate I-5.
The reaction time for the final step (conditions: THF, reflux temperature) was 13 days. Purification by column chromatography (silica gel, eluent: $CHCl_3$ plus isopropanol 10%→90%) gave 187 mg (25%) of the title compound (only eluted diastereomer).
¹H-NMR: diastereomer 1
¹H-NMR (DMSO-d₆): δ 8.10–8.04 (m, 2H), 7.55–7.51 (m, 3H), 7.38 (t, 2H), 7.18–7.13 (m, 2H), 7.03–6.99 (m, 2H), 5.53 (m, 1H), 3.95–3.70 (m, 3H), 3.65–3.35 (m, 3H), 3.16 (m, 2H), 2.99 (s, 3H), 2.79–2.64 (m, 1H), 2.22–2.02 (m, 3H).
MS [M−Cl]⁺: 488

(* Configuration not assigned)

EXAMPLE 17

(1*,3S)-1-[3-(4-Fluorophenoxy)propyl]-3-(2-hydroxy-2,2-dithien-2-ylacetoxy)-1-methylpyrrolidinium chloride (diastereomer 1)

The title compound was obtained as a single isomer according to method (b) from Intermediate I-6.
The reaction time for the final step (conditions: THF, reflux temperature) was 11 days. Purification by column chromatography (silica gel, eluent: $CHCl_3$ plus isopropanol 10%→85%) gave 309 mg (41.5%) of the title compound (first eluted diastereomer).
¹H-NMR: diastereomer 1 (diastereomer 2 not observed)
¹H-NMR (DMSO-d₆): δ 7.54–7.51 (m, 3H), 7.17–7.11 (m, 4H), 7.03–6.93 (m, 4H), 5.53 (m, 1H), 4.02 (t, 2H), 3.95–3.38 (m, 6H), 2.98 (s, 3H), 2.80–2.67 (m, 1H), 2.24–2.12 (m, 3H).
MS [M−Cl]⁺: 476.

(* Configuration not assigned)

EXAMPLE 18

(1*,3S)-1-[3-(4-Fluorophenoxy)propyl]-3-(2-hydroxy-2,2-dithien-2-ylacetoxy)-1-methylpyrrolidinium chloride (diastereomer 2)

The title compound was obtained as a single isomer according to method (b) from Intermediate I-6.
The reaction time for the final step (conditions: THF, reflux temperature) was 11 days. Purification by column chromatography (silica gel, eluent: $CHCl_3$ plus isopropanol 10%→85%) gave 62 mg (8.5%) of the title compound (second eluted diastereomer).
¹H-NMR: diastereomer 2 (diastereomer 1 not observed).
¹H-NMR (DMSO-d₆): δ 7.49–7.47 (m, 3H), 7.19–7.10 (m, 4H), 6.99–6.92 (m, 4H), 5.54 (m, 1H), 3.98–3.88 (m, 3H), 3.75–3.61 (m, 3H), 3.50–3.40 (m, 2H), 3.14 (s, 3H), 2.79–2.64 (m, 1H), 2.23–2.06 (m, 3H).

MS [M−Cl]⁺: 476.

(* Configuration not assigned)

EXAMPLE 19

(1*,3S)-3-(2-Hydroxy-2,2-dithien-2-ylacetoxy)-1-methyl-1-(3-phenylpropyl)pyrrolidinium bromide (diastereomer 1)

The title compound was obtained as a single isomer according to method (b) from Intermediate I-6.

The reaction time for the final step (conditions: THF, reflux temperature) was 8 days.

Purification by column chromatography (silica gel, eluent: CHCl₃ plus isopropanol 10%→60%) gave 250 mg (31.2%) of the title compound (first eluted diastereomer).

¹H-NMR: diastereomer 1 (diastereomer 2 not observed).
¹H-NMR (DMSO-d₆): δ 7.46–7.44 (m, 3H), 7.29–7.13 (m, 5H), 7.10–7.05 (m, 2H), 6.96–6.92 (m, 2H), 5.45 (m, 1H), 3.85–3.77 (m, 1H), 3.71–3.31 (m, 5H), 2.87 (s, 3H), 2.71–2.58 (m, 1H), 2.54 (t, 2H), 2.13–1.90 (m, 3H).

MS [M−Br]⁺: 442

(* Configuration not assigned)

EXAMPLE 20

(1*,3S)-3-(2-Hydroxy-2,2-dithien-2-ylacetoxy)-1-methyl-1-(3-phenylpropyl)pyrrolidinium bromide (diastereomer 2)

The title compound was obtained as a single isomer according to method (b) from Intermediate I-6.

The reaction time for the final step (conditions: THF, reflux temperature) was 8 days. Purification by column chromatography (silica gel, eluent: CHCl₃ plus isopropanol 10%→60%) gave 169 mg (20.8%) of the title compound (second eluted diastereomer).

¹H-NMR: diastereomer 2 (diastereomer 1 not observed).
¹H-NMR (DMSO-d₆): δ 7.54–7.51 (m, 2H), 7.50 (s, OH, 1H), 7.36–7.22 (m, 5H), 7.16 (dd, 1H), 7.11 (dd, 1H), 7.03–6.98 (m, 2H), 5.53 (m, 1H), 3.93–3.85 (m, 1H), 3.73–3.24 (m, 5H), 3.09 (s, 3H), 2.77–2.62 (m, 1H), 2.55–2.45 (m, 2H), 2.18–2.09 (m, 1H), 2.03–1.89 (m, 2H).

MS [M−Br]⁺: 442.

(* Configuration not assigned)

EXAMPLE 21

(3R)-1-(2-Benzyloxyethyl)-3-(2-cyclohexyl-2-fur-2-yl-2-hydroxyacetoxy)-1-methylpyrrolidinium bromide (mixture 1 of stereoisomers)

The title compound was obtained as a mixture of stereoisomers according to method (b) from Intermediate I-11.

The reaction time for the final step (conditions: THF, reflux temperature) was 5 days. Purification by column chromatography (silica gel, eluent: CHCl₃ plus isopropanol 10%→50%) gave 169 mg (53.0%) of the title compound (first eluted mixture of stereoisomers).

¹H-NMR: mixture 1 of stereoisomers
¹H-NMR (DMSO-d₆): δ 7.62 (m, 1H), 7.37–7.32 (m, 5H), 6.43–6.39 (m, 2H), 6.01 (s, OH, 1H), 5.43 (m, 1H), 4.54 (m, 2H), 3.94–3.20 (m, 8H), 3.10–3.05 (d, 3H), 2.76–2.62 (m, 1H), 2.24–1.90 (m, 2H), 1.74–1.57 (m, 3H), 1.37–1.11 (m, 7H).

MS [M−Br]⁺: 442.

EXAMPLE 22

(3R)-1-(2-Benzyloxyethyl)-3-(2-cyclohexyl-2-fur-2-yl-2-hydroxyacetoxy)-1-methylpyrrolidinium bromide (mixture 2 of stereoisomers)

The title compound was obtained as a mixture of stereoisomers according to method (b) from Intermediate I-11.

The reaction time for the final step (conditions: THF, reflux temperature) was 5 days. Purification by column chromatography (silica gel, eluent: CHCl₃ plus isopropanol 10%→50%) gave 125 mg (40.0%) of the title compound (second eluted mixture of stereoisomers).

¹H-NMR: mixture 2 of stereoisomers.
¹H-NMR (DMSO-d₆): δ 7.58 (s, 1H), 7.35 (m, 5H), 6.39 (m, 2H), 6.00 (s, OH, 1H), 5.44 (m, 1H), 4.55 (m, 2H), 3.91–3.20 (m, 8H), 3.20–3.04 (m, 3H), 2.65 (m, 1H), 2.23–1.86 (m, 2H), 1.65 (m, 3H), 1.38–1.06 (m, 7H).

MS [M−Br]⁺: 442.

EXAMPLE 23

(1*,3R)-3-[(2R)-2-Cyclopentyl-2-hydroxy-2-phenylacetoxy]-1-methyl-1-(3-phenoxypropyl)pyrrolidinium bromide (diastereomer 1)

The title compound was obtained as a single isomer according to method (b) from Intermediate I-13.

The reaction time for the final step (conditions: THF, reflux temperature) was 63 hours. Purification by column chromatography (silica gel, eluent: CH₂Cl₂ plus isopropanol 10%→30%) gave 248 mg (36.6%) of the title compound (first eluted diastereomer).

¹H-NMR: diastereomer 1 (diastereomer 2 not observed)
¹H-NMR (DMSO-d₆): δ 7.59 (d, 2H), 7.38–7.28 (m, 5H), 6.98–6.91 (m, 3H), 5.85 (s, OH, 1H), 5.38 (m, 1H), 4.04 (t, 2H), 3.91–3.51 (m, 6H), 3.05 (s, 3H), 2.98–2.84 (m, 1H), 2.71–2.61 (m, 1H), 2.25–2.07 (m, 3H), 1.59–1.16 (m, 8H).

MS [M−Br]⁺: 438

(* Configuration not assigned)

EXAMPLE 24

(1*,3R)-3-[(2R)-2-Cyclopentyl-2-hydroxy-2-phenylacetoxy]-1-methyl-1-(3-phenoxypropyl)pyrrolidinium bromide (diastereomer 2)

The title compound was obtained as a single isomer according to method (b) from Intermediate I-13.

The reaction time for the final step (conditions: THF, reflux temperature) was 63 hours. Purification by column chromatography (silica gel, eluent: CH₂Cl₂ plus isopropanol 10%→30%) gave 428 mg (62.4%) of the title compound (second eluted diastereomer).

¹H-NMR: diastereomer 2 (diastereomer 1 not observed).
¹H-NMR (DMSO-d₆): δ 7.57 (d, 2H), 7.36–7.18 (m, 5H), 7.00–6.94 (m, 3H), 5.84 (s, OH, 1H), 5.40 (m, 1H), 4.05–3.42 (m, 8H), 3.13 (s, 3H), 2.92–2.83 (m, 1H), 2.72–2.63 (m, 1H), 2.20–2.08 (m, 3H), 1.57–1.13 (m, 8H).

MS [M−Br]⁺: 438

(* Configuration not assigned)

EXAMPLE 25

(1*,3R)-1-[3-(Benzo[1,3]dioxol-5-yloxy)propyl]-1-methyl-3-[(9H-xanthen-9-ylcarbonyl)oxy]pyrrolidinium bromide (diastereomer 1)

The title compound was obtained as a single isomer according to method (b) from Intermediate I-8.

The reaction time for the final step (conditions: THF, reflux temperature) was 13 days. Purification by column chromatography (silica gel, eluent: $CHCl_3$ plus isopropanol 20%→40%) gave 219 mg (29.7%) of the title compound (first eluted diastereomer).

$^1$H-NMR: diastereomer 1 (diastereomer 2 not observed).

$^1$H-NMR (DMSO-$d_6$): δ 7.47 (d, 2H), 7.41–7.33 (m, 2H), 7.21–7.13 (m, 4H), 6.82 (d, 1H), 6.63 (d, 1H), 6.37 (dd, 1H), 5.96 (s, 2H), 5.34 (m, 1H), 5.29 (s, 1H), 3.97–3.50 (m, 8H), 2.95 (s, 3H), 2.67–2.57 (m, 1H), 2.18–2.00 (m, 3H).

MS [M−Br]$^+$: 488

(* Configuration not assigned)

EXAMPLE 26

(1*,3R)-1-[3-(Benzo[1,3]dioxol-5-yloxy)propyl]-1-methyl-3-[(9H-xanthen-9-ylcarbonyl)oxy]pyrrolidinium bromide (diastereomer 2)

The title compound was obtained as a single isomer according to method (b) from Intermediate I-8.

The reaction time for the final step (conditions: THF, reflux temperature) was 13 days. Purification by column chromatography (silica gel, eluent: $CHCl_3$ plus isopropanol 20%→40%) gave 443 mg (60.3%) of the title compound (second eluted diastereomer).

$^1$H-NMR: diastereomer 2 (diastereomer 1 not observed)

$^1$H-NMR (DMSO-$d_6$): δ 7.45–7.31 (m, 4H), 7.18–7.09 (m, 4H), 6.86 (d, 1H), 6.69 (d, 1H), 6.44 (dd, 1H), 5.97 (s, 2H), 5.35 (m, 1H), 5.25 (s, 1H), 3.99–3.82 (m, 3H), 3.66–3.40 (m, 5H), 3.11 (s, 3H), 2.66–2.58 (m, 1H), 2.12–1.99 (m, 3H).

MS [M−Br]$^+$: 488

(* Configuration not assigned)

EXAMPLE 27

(1*,3S)-1-Methyl-1-(3-o-tolyloxypropyl)-3-[(9H-xanthen-9-ylcarbonyl)oxy]pyrrolidinium bromide (diastereomer 1)

The title compound was obtained as a single isomer according to method (b) from Intermediate I-9.

The reaction time for the final step (conditions: THF, reflux temperature) was 4 days. Purification by column chromatography (silica gel, eluent: $CHCl_3$ plus isopropanol 10%→40%) gave 461 mg (37.8%) of the title compound (first eluted diastereomer).

$^1$H-NMR: diastereomer 1 (diastereomer 2 not observed).

$^1$H-NMR (DMSO-$d_6$): δ 7.48–7.34 (m, 4H), 7.22–7.12 (m, 6H), 6.93–6.81 (m, 2H), 5.35 (m, 1H), 5.29 (s, 1H), 4.02 (t, 2H), 3.85–3.69 (m, 3H), 3.59–3.51 (m, 3H), 2.96 (s, 3H), 2.69–2.58 (m, 1H), 2.24–2.02 (m, 3H), 2.16 (s, 3H).

MS [M−Br]$^+$: 458

(* Configuration not assigned)

EXAMPLE 28

(1*,3S)-1-Methyl-1-(3-o-tolyloxypropyl)-3-[(9H-xanthen-9-ylcarbonyl)oxy]pyrrolidinium bromide (diastereomer 2)

The title compound was obtained as a single isomer according to method (b) from Intermediate I-9.

The reaction time for the final step (conditions: THF, reflux temperature) was 4 days. Purification by column chromatography (silica gel, eluent: $CHCl_3$ plus isopropanol 10%→40%) gave 704 mg (59.2%) of the title compound (second eluted diastereomer).

$^1$H-NMR: diastereomer 2 (diastereomer 1 not observed)

$^1$H-NMR (DMSO-$d_6$): δ 7.44–7.41 (m, 2H), 7.34–7.24 (m, 2H), 7.21–7.07 (m, 6H), 6.99 (d, 1H), 6.89 (t, 1H), 5.37 (m, 1H), 5.25 (s, 1H), 4.01 (t, 2H), 3.94–3.85 (m, 1H) 3.69–3.63 (m, 3H), 3.48–3.41 (m, 2H), 3.13 (s, 3H), 2.71–2.56 (m, 1H), 2.19 (s, 3H), 2.19–2.00 (m, 3H).

MS [M−Br]$^+$: 458

(* Configuration not assigned)

EXAMPLE 29

Described in Method (b)

(3R)-3-{[(9-hydroxy-9H-fluoren-9-yl)carbonyl]oxy}-1-methyl-1-(4-oxo-4-phenylbutyl)pyrrolidinium formate 0.575 g (1.858 mmol) of 9-Hydroxy-9H-fluorene-9-carboxylic acid (3R)-1-methylpyrrolidin-3-yl ester (Intermediate I-10) and 1.018 g (5.576 mmol) of 4-chloro-1-phenylbutan-1-one in 6 ml of THF were refluxed for 20 days. After this time THF was poured off, and the residue was washed with THF in order to eliminate the alkylating agent. The product obtained (234 mg) was purified by preparative HPLC-MS to give 65 mg (7%) of the title compound (mixture of two stereoisomers) as a formate.

MS [M−HCOO$^-$]$^+$: 456.

Conditions used in the purification HPLC-MS:

Column: Symmetry C18, 100 A, 5 μm 19×100 mm, Waters.

Mobile phase: A ($H_2O$ 0.1% $HCOONH_4$, pH=3) and B (AcN 0.1% $HCOONH_4$, pH=3)

EXAMPLE 30

(3R)-3-(2-Cyclohexyl-2-fur-2-yl-2-hydroxyacetoxy)-1-methyl-1-[3-(methylphenylamino)propyl]pyrrolidinium chloride (mixture 1 of stereoisomers)

The title compound was obtained as a mixture of stereoisomers according to method (b) from Intermediate I-11.

The reaction time for the final step (conditions: THF, reflux temperature) was 27 days. Purification by column chromatography (silica gel, eluent $CHCl_3$ plus isopropanol 5%→50%) gave 130 mg (27%) of the title product (first eluted mixture of stereoisomers).

$^1$H-NMR: mixture 1 of stereoisomers $^1$H-NMR (DMSO-$d_6$): δ 7.62 (s, 1H), 7.21–7.15 (m, 2H), 6.74 (d, 2H), 6.64 (t, 1H), 6.42–6.39 (m, 2H), 6.00 (s, OH, 1H), 5.43 (m, 1H), 3.90–3.30 (m, 6H), 3.05–3.01 (two singlets, 3H), 2.88 (s, 3H), 2.73–2.59 (m, 1H), 2.25–1.85 (m, 4H), 1.73–1.57 (m, 3H), 1.37–1.06 (m, 7H).

MS [M−Cl]$^+$: 455

EXAMPLE 31

(3R)-3-(2-Cyclohexyl-2-fur-2-yl-2-hydroxyacetoxy)-1-methyl-1-[3-(methylphenylamino)propyl]pyrrolidinium chloride (mixture 2 of stereoisomers)

The title compound was obtained as a mixture of stereoisomers according to method (b) from Intermediate I-11.

The reaction time for the final step (conditions: THF, reflux temperature) was 27 days. Purification by column chromatography (silica gel, eluent $CHCl_3$ plus isopropanol 5%→50%) gave 125 mg (26%) of the title product (second eluted mixture of stereoisomers).

$^1$H-NMR: mixture 2 of stereoisomers $^1$H-NMR (DMSO-$d_8$): δ 7.60 (s, 1H), 7.22–7.16 (m, 2H), 6.75 (d, 2H), 6.64 (t, 1H), 6.41 (m, 2H), 6.07 (m, OH, 1H), 5.44 (m, 1H), 3.94–3.85 (m, 1H), 3.75–3.32 (m, 5H), 3.10 (s, 3H), 2.90 (s, 3H), 2.72–2.60 (m, 1H), 2.25–1.85 (m, 4H), 1.73–1.57 (m, 3H), 1.02 (m, 7H).

MS [M−Cl]$^+$: 455

EXAMPLE 32

(3R)-1-[3-(Benzothiazol-2-yloxy)propyl]-3-(2-cyclohexyl-2-fur-2-yl-2-hydroxyacetoxy)-1-methylpyrrolidinium chloride (mixture 1 of stereoisomers)

The title compound was obtained as a mixture of stereoisomers according to method (b) from Intermediate I-11.

The reaction time for the final step (conditons: THF, reflux temperature) was 26 days. Purification by column chromatography (silica gel, eluent $CHCl_3$ plus isopropanol 10%→70%) gave 46 mg (9.13%) of the title product (first eluted mixture of stereoisomers).

$^1$H-NMR: mixture 1 of stereoisomers $^1$H-NMR (DMSO-$d_6$): δ 7.70 (d, 1H), 7.60 (s, 1H), 7.46–7.39 (m, 2H), 7.27–7.21 (m, 1H), 6.39 (m, 2H), 5.99 (s, OH, 1H), 5.43 (m, 1H), 4.02 (t, 2H), 3.90–3.65 (m, 2H), 3.65–3.20 (m, 4H), 3.03–3.00 (two singlets, 3H), 2.75–2.55 (m, 1H), 2.25–1.90 (m, 4H), 1.80–1.50 (m, 3H), 1.40–1.01 (m, 7H).

MS [M−Cl]$^+$: 499

EXAMPLE 33

(3R)-1-[3-(Benzothiazol-2-yloxy)propyl]-3-(2-cyclohexyl-2-fur-2-yl-2-hydroxyacetoxy)-1-methylpyrrolidinium chloride (mixture 2 of stereoisomers)

The title compound was obtained as a mixture of stereoisomers according to method (b) from Intermediate I-11.

The reaction time for the final step (conditions: THF, reflux temperature) was 26 days. Purification by column chromatography (silica gel, eluent $CHCl_3$ plus isopropanol 10%→70%) gave 167 mg (32.37%) of the title product (second eluted mixture of stereoisomers).

$^1$H-NMR: mixture 2 of stereoisomers $^1$H-NMR (DMSO-$d_6$): δ 7.69 (d, 1H), 7.60 (m, 1H), 7.49–7.38 (m, 2H), 7.27–7.20 (m, 1H), 6.39 (m, 2H), 6.01 (s, OH 1H), 5.42 (m, 1H), 4.02 (m, 2H), 3.90–3.65 (m, 2H), 3.65–3.45 (m, 2H), 3.45–3.30 (m, 2H), 3.04–3.00 (two singlets, 3H), 2.75–2.55 (m, 1H), 2.25–1.85 (m, 4H), 1.73–1.56 (m, 3H), 1.35–1.01 (m, 7H).

MS [M−Cl]$^+$: 499

EXAMPLE 34

(3R)-1-[3-(Benzothiazol-2-yloxy)propyl]-3-(2-cyclohexyl-2-fur-2-yl-2-hydroxyacetoxy)-1-methylpyrrolidinium chloride (mixture 3 of stereoisomers)

The title compound was obtained as a mixture of stereoisomers according to method (b) from Intermediate I-11.

The reaction time for the final step (conditions: THF, reflux temperature) was 26 days. Purification by column chromatography (silica gel, eluent $CHCl_3$ plus isopropanol 10%→70%) gave 220 mg (41.5%) of the title product (third eluted mixture of stereoisomers).

$^1$H-NMR: mixture 3 of stereoisomers $^1$H-NMR (DMSO-$d_8$): δ 7.71 (d, 1H), 7.60 (s, 1H), 7.52–7.38 (m, 2H), 7.25 (t, 1H), 6.41 (m, 2H), 6.07–6.04 (two singlets, OH, 1H), 5.43 (m, 1H), 4.03 (m, 2H), 3.95–3.86 (m, 1H), 3.69–3.30 (m, 5H), 3.08 (s, 3H), 2.64 (m, 1H), 2.25–1.90 (m, 4H), 1.72–1.56 (m, 3H), 1.40–1.02 (m, 7H).

MS [M−Cl]$^+$: 499

EXAMPLE 35

3-(2-Cyclohexyl-2-fur-2-yl-2-hydroxyacetoxy)-1-ethyl-1-(3-phenylsulfanylpropyl)pyrrolidinium bromide (mixture 1 of stereoisomers)

The title compound was obtained as a mixture of stereoisomers according to method (b) from Intermediate I-12.

The reaction time for the final step (conditions: THF, reflux temperature) was 14 days. Purification by column chromatography (silica gel, eluent $CHCl_3$ plus isopropanol 5%→15%) gave 153 mg (29.2%) of the title product (first eluted mixture of stereoisomers).

$^1$H-NMR: mixture 1 of stereoisomers $^1$H-NMR (DMSO-$d_6$): δ 7.63 (s, 1H), 7.40–7.32 (m, 4H), 7.25–7.20 (m, 1H), 6.43–6.38 (m, 2H), 5.99 (s, OH, 1H), 5.41 (m, 1H), 3.87–3.18 (m, 6H), 3.04 (m, 2H), 2.66–2.54 (m, 1H), 2.25–1.90 (m, 4H), 1.73–1.58 (m, 3H), 1.36–1.05 (m, 10H).

MS [M−Brl]$^+$: 472

EXAMPLE 36

3-(2-Cyclohexyl-2-fur-2-yl-2-hydroxyacetoxy)-1-ethyl-1-(3-phenylsulfanylpropyl)pyrrolidinium bromide (mixture 2 of stereoisomers)

The title compound was obtained as a mixture of stereoisomers according to method (b) from Intermediate I-12.

The reaction time for the final step (conditions: THF, reflux temperature) was 14 days. Purification by column chromatography (silica gel, eluent $CHCl_3$ plus isopropanol 5%→15%) gave 226 mg (43.8%) of the title product (second eluted mixture of stereoisomers).

$^1$H-NMR: mixture 2 of stereoisomers $^1$H-NMR (DMSO-$d_6$): δ 7.61 (s, 1H), 7.41–7.32 (m, 4H), 7.24 (m, 1H), 6.40 (m, 2H), 6.02–6.00 (two singlets, OH, 1H), 5.42 (m, 1H), 3.88–3.80 (m, 1H), 3.69–3.26 (m, 5H), 3.04 (m, 2H), 2.65–2.55 (m, 1H), 2.25–1.85 (m, 4H), 1.73–1.56 (m, 3H), 1.43–1.02 (m, 10H).

MS [M−Brl]$^+$: 472

EXAMPLE 37

(1*,3R)-1-[3-(Biphenyl-4-yloxy)propyl]-3[(2R)-2-cyclopentyl-2-hydroxy-2-phenylacetoxy]-1-methylpyrrolidinium chloride (diastereomer 1)

The title compound was obtained as a single isomer according to method (b) from Intermediate I-13.

The reaction time for the final step (conditions: THF, reflux temperature) was 4 days. Purification by column chromatography (silica gel, eluent CHCl$_3$ plus isopropanol 5%→20%) gave 81 mg (27.7%) of the title product (first eluted diastereomer).

$^1$H-NMR: diastereomer 1 (diastereomer 2 not observed)
$^1$H-NMR (DMSO-d$_8$): δ 7.61–7.58 (m, 6H), 7.42–7.24 (m, 6H), 7.02 (d, 2H), 5.82 (s, OH, 1H), 5.39 (m, 1H), 4.12–4.08 (m, 2H), 3.91–3.55 (m, 6H), 3.07 (s, 3H), 2.95–2.65 (m, 2H), 2.27–2.09 (m, 3H), 1.61–1.17 (m, 8H).
MS [M−Cl]$^+$: 514

(* Configuration not assigned)

EXAMPLE 38

(1*,3R)-1-[3-(Biphenyl-4-yloxy)propyl]-3-[(2R)-2-cyclopentyl-2-hydroxy-2-phenylacetoxy]-1-methylpyrrolidinium chloride (diastereomer 2)

The title compound was obtained as a single isomer according to method (b) from Intermediate I-13.

The reaction time for the final step (conditions: THF, reflux temperature) was 4 days. Purification by column chromatography (silica gel, eluent CHCl$_3$ plus isopropanol 5%→20%) gave 111 mg (38.3%) of the title product (second eluted diastereomer).

$^1$H-NMR: diastereomer 2 (diastereomer 1 not observed)
$^1$H-NMR (DMSO-d$_6$): δ 7.64–7.55 (m, 6H), 7.42 (t, 2H), 7.33–7.19 (m, 4H), 7.04 (d, 2H), 5.81 (s, OH, 1H), 5.40 (m, 1H), 4.10–4.06 (m, 2H), 3.90 (dd, 1H), 3.80–3.50 (m, 5H), 3.13 (s, 3H), 2.93–2.83 (m, 1H), 2.75–2.62 (m, 1H), 2.24–2.08 (m, 3H), 1.64–1.10 (m, 8H).
MS [M−Cl]$^+$: 514

(* Configuration not assigned)

EXAMPLE 39

(1*,3R)-3-[(2R)-2-Cyclopentyl-2-hydroxy-2-phenylacetoxy]-1-methyl-1-[3-(5,6,7,8-tetrahydronaphthalen-2-yloxy)propyl]pyrrolidinium bromide (diastereomer 1)

The title compound was obtained as a single isomer according to method (b) from Intermediate I-13.

The reaction time for the final step (conditions: THF, reflux temperature) was 5 days. Purification by column chromatography (silica gel, eluent CHCl$_3$ plus isopropanol 0%→30%) gave 93 mg (30.6%) of the title product (first eluted diastereomer).

$^1$H-NMR: diastereomer 1 (diastereomer 2 not observed).
$^1$H-NMR (DMSO-d$_6$): δ 7.58 (d, 2H), 7.34 (t, 2H), 7.28–7.23 (m, 1H), 6.94 (d, 1H), 6.67–6.61 (m, 2H), 5.81 (s, OH, 1H), 5.37 (m, 1H), 3.97 (t, 2H), 3.85 (dd, 1H), 3.79–3.30 (m, 5H), 3.04 (s, 3H), 2.90 (m, 1H), 2.67–2.62 (m, 5H), 2.16 (m, 3H), 1.70–1.23 (m, 12H).
MS [M−Br]$^+$: 492

(* Configuration not assigned)

EXAMPLE 40

(1*,3R)-3-[(2R)-2-Cyclopentyl-2-hydroxy-2-phenylacetoxy]-1-methyl-[3-(5,6,7,8-tetrahydronaphthalen-2-yloxy)propyl]pyrrolidinium bromide (diastereomer 2)

The title compound was obtained as a single isomer according to method (b) from Intermediate I-13.

The reaction time for the final step (conditions: THF, reflux temperature) was 5 days. Purification by column chromatography (silica gel, eluent CHCl$_3$ plus isopropanol 0%→30%) gave 163 mg (54.4%) of the title product (second eluted diastereomer).

$^1$H-NMR: diastereomer 2 (diastereomer 1 not observed)
$^1$H-NMR (DMSO-d$_6$): δ 7.55 (d, 2H), 7.29 (t, 2H), 7.23–7.19 (m, 1H), 6.96 (d, 1H), 6.68–6.63 (m, 2H), 5.80 (s, OH, 1H), 5.39 (m, 1H), 3.97 (t, 2H), 3.89 (dd, 1H), 3.78–3.30 (m, 5H), 3.11 (s, 3H), 2.87 (m, 1H), 2.68–2.63 (m, 3H), 2.19–2.06 (m, 3H), 1.70–1.03 (m, 12H).
MS [M−Br]$^+$: 492

(* Configuration not assigned)

EXAMPLE 41

3-[(2R)-2-Cyclopentyl-2-hydroxy-2-phenylacetoxy]-1-ethyl-1-[3-(4-methoxyphenoxy)propyl]pyrrolidinium bromide (mixture 1 of stereoisomers)

The title compound was obtained as a mixture of stereoisomers according to method (b) from Intermediate I-14.

The reaction time for the final step (conditions: THF, reflux temperature) was 19 days. Purification by column chromatography (silica gel, eluent CHCl$_3$ plus isopropanol 0%→20%) gave 202 mg (24.1%) of the title product (first eluted mixture of stereoisomers).

$^1$H-NMR: mixture 1 of steroisomers
$^1$H-NMR (DMSO-d$_6$): δ 7.58 (m, 2H), 7.39–7.24 (m, 3H), 6.86 (s, 4H), 5.84 (s, OH, 1H), 5.38 (m, 1H), 3.95 (t, 2H), 3.92–3.80 (m, 1H), 3.69 (s, 3H), 3.69–3.27 (m, 7H), 2.91 (m, 1H), 2.60 (m, 1H), 2.07 (m, 3H), 1.59–1.11 (m, 11H).
MS [M−Br]$^+$: 482

EXAMPLE 42

3-[(2R)-2-Cyclopentyl-2-hydroxy-2-phenylacetoxy]-1-ethyl-1-[3-(4-methoxyphenoxy)propyl]pyrrolidinium bromide (mixture 2 of stereoisomers)

The title compound was obtained as a mixture of stereoisomers according to method (b) from Intermediate I-14.

The reaction time for the final step (conditions: THF, reflux temperature) was 19 days. Purification by column chromatography (silica gel, eluent CHCl$_3$ plus isopropanol 0%→20%) gave 384 mg (46.9%) of the title product (second eluted mixture of stereoisomers).

$^1$H-NMR: mixture 2 of steroisomers
$^1$H-NMR (DMSO-d$_6$): δ 7.57 (d, 2H), 7.35–7.20 (m, 3H), 6.88 (s, 4H), 5.86 (s, OH, 1H), 5.39 (m, 1H), 3.98–3.84 (m, 3H), 3.69 (s, 3H), 3.74–3.30 (m, 7H), 2.88 (m, 1H), 2.59 (m, 1H), 2.13–1.96 (m, 3H), 1.56–1.12 (m, 11H).
MS [M−Br]$^+$: 482

EXAMPLE 43

(3R)-1-[4-(4-Fluorophenyl)-4-oxobutyl]-3-(2-hydroxy-2,2-dithien-2-ylacetoxy)-1-methylpyrrolidinium formate The title compound was obtained as a mixture of two stereoisomers according to method (b) from Intermediate I-5.

The reaction time for the final step (conditions: THF, reflux temperature) was 24 days. After this time THF was poured off, and the residue was washed with THF in order to eliminate the alkylating agent. The product obtained (88 mg) was purified by preparative HPLC-MS (using the conditions described in Example 29) to give 30.1 mg of the title compound (mixture of two stereoisomers).

MS [M−HCOO⁻]⁺: 488

EXAMPLE 44

(3S)-3-(2-Hydroxy-2,2-dithien-2-ylacetoxy)-1-[3-(3-hydroxyphenoxy)propyl]-1-methylpyrrolidinium formate The title compound was obtained as a mixture of two stereoisomers according to method (b) from Intermediate I-6.

The reaction time for the final step (conditions: THF, reflux temperature) was 19 days. After this time, THF was evaporated, and a portion of the obtained residue was purified by preparative HPLC-MS (using the conditions described in Example 29) to give 5.0 mg of the title compound (mixture of two stereoisomers).

MS [M−HCOO⁻]⁺: 474

EXAMPLE 45

(3R)-1-[3-(3-Cyanophenoxy)propyl]-3-(2-cyclohexyl-2-fur-2-yl-2-hydroxyacetoxy)-1-methylpyrrolidinium formate The title compound was obtained as a mixture of stereoisomers according to method (b) from Intermediate I-11.

The reaction time for the final step (conditions: THF, reflux temperature) was 25 days. After this time, THF was evaporated, and a portion of the obtained residue was purified by preparative HPLC-MS (using the conditions described in Example 29) to give 65.6 mg of the title compound (mixture of stereoisomers).

MS [M−HCOO⁻]⁺: 467

EXAMPLE 46

(3R)-3-(2-Cyclohexyl-2-fur-2-yl-2-hydroxyacetoxy)-1-methyl-1-[3-(naphthalen-1-yloxy)propyl]pyrrolidinium formate The title compound was obtained as a mixture of stereoisomers according to method (b) from Intermediate I-11.

The reaction time for the final step (conditions: THF, reflux temperature) was 25 days. After this time, THF was evaporated, and a portion of the obtained residue was purified by preparative HPLC-MS (using the conditions described in Example 29) to give 13.9 mg of the title compound (mixture of stereoisomers).

MS [M−HCOO⁻]⁺: 492

The following examples illustrate pharmaceutical compositions according to the present invention and procedures for their preparation.

EXAMPLE 47

Preparation of a Pharmaceutical Composition: Tablets

Formulation:

| | |
|---|---|
| Compound of the present invention | 5.0 mg |
| Lactose | 113.6 mg |
| Microcrystalline cellulose | 28.4 mg |
| Light silicic anhydride | 1.5 mg |
| Magnesium stearate | 1.5 mg |

Using a mixer machine, 15 g of the compound of the present invention was mixed with 340.8 g of lactose and 85.2 g of microcrystalline cellulose. The mixture was subjected to compression moulding using a roller compactor to give a flake-like compressed material. The flake-like compressed material was pulverized using a hammer mill, and the pulverized material was screened through a 20 mesh screen. A 4.5 g portion of light silicic anhydride and 4.5 g of magnesium stearate were added to the screened material and mixed. The mixer product was subjected to a tablets making machine equipped with a die/punch system of 7.5 mm in diameter, thereby obtaining 3,000 tablets each having 150 mg in weight.

EXAMPLE 48

Preparation of a Pharmaceutical Composition: Coated Tablets

Formulation:

| | |
|---|---|
| Compound of the present invention | 5.0 mg |
| Lactose | 95.2 mg |
| Corn starch | 40.8 mg |
| Polyvinylpyrrolidone K25 | 7.5 mg |
| Magnesium stearate | 1.5 mg |
| Hydroxypropylcellulose | 2.3 mg |
| Polyethylene glycol 6000 | 0.4 mg |
| Titanium dioxide | 1.1 mg |
| Purified talc | 0.7 mg |

Using a fluidized bed granulating machine, 15 g of the compound of the present invention was mixed with 285.6 g of lactose and 122.4 g of corn starch. Separately, 22.5 g of polyvinylpyrrolidone was dissolved in 127.5 g of water to prepare a binding solution. Using a fluidized bed granulating machine, the binding solution was sprayed on the above mixture to give granulates. A 4.5 g portion of magnesium stearate was added to the obtained granulates and mixed. The obtained mixture was subjected to a tablet making machine equipped with a die/punch biconcave system of 6.5 mm in diameter, thereby obtaining 3,000 tablets, each having 150 mg in weight.

Separately, a coating solution was prepared by suspending 6.9 g of hydroxypropylmethylcellulose 2910, 1.2 g of polyethylene glycol 6000, 3.3 g of titanium dioxide and 2.1 g of purified talc in 72.6 g of water. Using a High Coated, the 3,000 tablets prepared above were coated with the coating solution to give film-coated tablets, each having 154.5 mg in weight.

EXAMPLE 49

Preparation of a Pharmaceutical Composition: Liquid Inhalant

Formulation:

| | |
|---|---|
| Compound of the present invention | 400 μg |
| Physiological saline | 1 ml |

A 40 mg portion of the compound of the present invention was dissolved in 90 ml of physiological saline, and the solution was adjusted to a total volume of 100 ml with the same saline solution, dispensed in 1 ml portions into 1 ml capacity ampoule and then sterilized at 115° C. for 30 minutes to give a liquid inhalant.

EXAMPLE 50

Preparation of a Pharmaceutical Composition: Powder Inhalant

Formulation:

| | |
|---|---|
| Compound of the present invention | 200 μg |
| Lactose | 4,000 μg |

A 20 g portion of the compound of the present invention was uniformly mixed with 400 g of lactose, and a 200 mg portion of the mixture was packed in a powder inhaler for exclusive use to produce a powder inhalant.

EXAMPLE 51

Preparation of a Pharmaceutical Composition: Inhalation Aerosol

Formulation:

| | |
|---|---|
| Compound of the present invention | 200 μg |
| Dehydrated (Absolute) ethyl alcohol USP | 8,400 μg |
| 1,1,1,2-Tetrafluoroethane (HFC-134A) | 46,810 μg |

The active ingredient concentrate is prepared by dissolving 0.0480 g of the compound of the present invention in 2.0160 g of ethyl alcohol. The concentrate is added to an appropriate filling apparatus. The active ingredient concentrate is dispensed into aerosol container, the headspace of the container is purged with Nitrogen or HFC-134A vapor (purging ingredients should not contain more than 1 ppm oxygen) and is sealed with valve. 11.2344 g of HFC-134A propellant is then pressure filled into the sealed container.

The invention claimed is:

1. A compound of formula (I):

(I)

[Structure: R1, R2, R3 substituted ring B—(CH$_2$)$_n$—A—(CH$_2$)$_m$—N$^+$(R4)(pyrrolidine with O-C(=O)-D), X$^-$]

wherein

B represents a group chosen from phenyl, naphthalenyl, 5,6,7,8-tetrahydronaphthalenyl, benzo[1,3]dioxolyl, biphenyl, and a 5 to 10-membered heteroaromatic group containing one or more heteroatoms chosen from N, O and S;

$R^1$, $R^2$ and $R^3$ each independently represent a group chosen from a hydrogen atom, a halogen atom, hydroxy, phenyl, —OR$^5$, —SR$^5$, —NR$^5$R$^6$, —NHCOR$^5$, —CONR$^5$R$^6$, —CN, —NO$_2$, —COOR$^5$, —CF$_3$, a straight optionally substituted lower alkyl group, and a branched optionally substituted lower alkyl group;

or $R^1$ and $R^2$ together form an aromatic or alicyclic ring or a heterocyclic group;

$R^5$ and $R^6$ each independently represent a group chosen from a hydrogen atom, a straight optionally substituted lower alkyl group and a branched optionally substituted lower alkyl group, or $R^5$ and $R^6$ together form an alicyclic ring;

n is an integer from 0 to 4;

A represents a group chosen from O—, —S—, —S(O)—, and —S(O)$_2$—;

m is an integer from 0 to 8;

$R^4$ represents a lower alkyl group;

D represents a group of formula i)

i)

[Structure: central C with R9, R10, R11 substituents]

wherein $R^9$ represents a group chosen from phenyl, 2-furyl, 3-furyl, 2-thienyl and 3-thienyl;

$R^{10}$ represents a group chosen from phenyl, 2-furyl, 3-furyl, 2-thienyl, 3-thienyl and C$_3$–C$_7$ cycloalkyl;

and $R^{11}$ represents a group chosen from a hydrogen atom, hydroxy, methyl, or - and CH$_2$OH;

wherein each of the cyclic groups represented by $R^9$ and $R^{10}$ is independently optionally substituted by one or two substituents chosen from halogen, straight optionally substituted lower alkyl, branched optionally substituted lower alkyl, hydroxy, optionally substituted lower alkoxy, nitro, cyano, —CO$_2$R$^{12}$ and —NR$^{12}$R$^{13}$, wherein $R^{12}$ and $R^{13}$ are identical or different and each independently chosen from a hydrogen atom, straight optionally substituted lower alkyl groups and branched optionally substituted lower alkyl groups; and X$^-$ represents a pharmaceutically acceptable anion of a mono or polyvalent acid;

or an individual stereoisomers of a compound of formula (I) or mixture of stereoisomers of a compound of formula (I);

with the proviso that in those compounds of formula (I) wherein B is phenyl, $R^9$ is unsubstituted phenyl, $R^{10}$ is unsubstituted phenyl or unsubstituted $C_3$–$C_7$ cycloalkyl, and $R^{11}$ is hydrogen or hydroxy, the sequence —$(CH_2)_n$—A—$(CH_2)_m$— is not one of methylene, ethylene or propylene.

2. A compound according to claim 1, wherein B represents a group chosen from phenyl, pyrrolyl, thienyl, furyl, biphenyl, naphthalenyl, 5,6,7,8-tetrahydronaphthalenyl, benzo[1,3]dioxolyl, imidazolyl and benzothiazolyl.

3. A compound according to claim 2, wherein B represents a group chosen from phenyl, thienyl and pyrrolyl.

4. A compound according to claim 1, wherein $R^1$, $R^2$ and $R^3$ each independently represents a group chosen from a hydrogen atom, a halogen atom, hydroxy, methyl, tert-butyl, —$CH_2OH$, 3-hydroxypropyl, —OMe, —$NMe_2$, —NHCOMe, —$CONH_2$, —CN, —$NO_2$, —COOMe and —$CF_3$.

5. A compound according to claim 4, wherein $R^1$, $R^2$ and $R^3$ each independently represents a group chosen from hydrogen, fluorine, chlorine and hydroxy.

6. A compound according to claim 1, wherein n=0 or 1; m is an integer from 1 to 6; and A represents a group chosen from —O— and —S—.

7. A compound according to claim 6, wherein A is —O—.

8. A compound according to claim 6, wherein the pyrrolidinium group is substituted on the nitrogen atom with a $C_1$–$C_4$ alkyl group and another group chosen from 3-phenoxypropyl, 2-phenoxyethyl, 3-(3-hydroxyphenoxy)propyl, 3-(4-fluorophenoxy)propyl, 2-benzyloxyethyl, 3-o-tolyloxypropyl, 3-(3-cyanophenoxy)propyl, 3-phenylsulphanylpropyl, 3-(2-chlorophenoxy)propyl, 3-(2,4-difluorophenoxy)propyl, 3-(4-methoxyphenoxy)propyl, and 3-(benzo[1,3]dioxol-5-yloxy)propyl.

9. A compound according to claim 8 wherein the pyrrolidinium group is substituted on the nitrogen atom with a $C_1$–$C_4$ alkyl group and another group chosen from 3-phenoxypropyl, 2-phenoxyethyl, 3-(3-hydroxyphenoxy)propyl, and 3-(4-fluorophenoxy)propyl.

10. A compound according to claim 1, wherein D is a group of formula i), and wherein $R^9$ is a group chosen from phenyl, 2-thienyl and 2-furyl; $R^{10}$ is a group chosen from phenyl, 2-thienyl, cyclohexyl and cyclopentyl; and $R^{11}$ is a hydroxy group.

11. A compound according to claim 1, wherein $X^-$ is chosen from chloride, bromide, trifluoroacetate and methanesulphonate.

12. A compound according to claim 1, wherein the carbon at the 3-position of the pyrrolidinium ring has a R configuration.

13. A compound according to claim 1, wherein the carbon at the 3-position of the pyrrolidinium ring has a S configuration.

14. A compound according to claim 1, wherein D is a group of formula i) and the carbon substituted by $R^9$, $R^{10}$ and $R^{11}$ has a R configuration.

15. A compound according to claim 1, wherein D is a group of formula i) and the carbon substituted by $R^9$, $R^{10}$ and $R^{11}$ has a S configuration.

16. A compound according to claim 1 wherein said compound is a single isomer.

17. A compound according to claim 1 chosen from:
3-(2-Hydroxy-2,2-dithien-2-ylacetoxy)-1-methyl-1-(2-phenoxyethyl)pyrrolidinium bromide;
3-(2-Hydroxy-2,2-dithien-2-ylacetoxy)-1-methyl-1-(3-phenoxypropyl)pyrrolidinium bromide;
1-Ethyl-3-(2-Hydroxy-2,2-dithien-2-ylacetoxy)-1-[3-(3-hydroxyphenoxy)propyl]pyrrolidinium trifluoroacetate;
3-(2-Hydroxy-2,2-dithien-2-ylacetoxy)-1-methyl-1-[6-(4-phenylbutoxy)hexyl]pyrrolidinium trifluoroacetate;
1-(2-Benzyloxyethyl)-3-(2-cyclohexyl-2-fur-2-yl-2-hydroxyacetoxy)-1-methylpyrrolidinium trifluoroacetate;
1-[3-(3-Cyanophenoxy)propyl]-3-(2-cyclohexyl-2-fur-2-yl-2-hydroxyacetoxy)-1-methylpyrrolidinium trifluoroacetate;
3-(2-Cyclohexyl-2-fur-2-yl-2-hydroxyacetoxy)-1-methyl-1-[3-(naphthalen-1-yloxy)propyl]pyrrolidinium trifluoroacetate;
3-(2-Cyclohexyl-2-fur-2-yl-2-hydroxyacetoxy)-1-ethyl-1-(3-phenylsulphanylpropyl)pyrrolidinium trifluoroacetate;
1-[3-(Benzothiazol-2-yloxy)propyl]-3-(2-cyclohexyl-2-fur-2-yl-2-hydroxyacetoxy)-1-methylpyrrolidinium trifluoroacetate;
3-(2-Cyclopentyl-2-hydroxy-2-phenylacetoxy)-1-methyl-1-(3-phenoxypropyl)pyrrolidinium bromide;
3-(2-Cyclopentyl-2-hydroxy-2-phenylacetoxy)-1-methyl-1-[3-(2,4,6-trimethylphenoxy)propyl]pyrrolidinium trifluoroacetate;
1-[3-(2-Chlorophenoxy)propyl]-3-(2-cyclopentyl-2-hydroxy-2-phenylacetoxy)-1-methylpyrrolidinium trifluoroacetate;
3-(2-Cyclopentyl-2-hydroxy-2-phenylacetoxy)-1-methyl-1-[3-(3-trifluoromethylphenoxy)propyl]pyrrolidinium trifluoroacetate;
1-[3-(Biphenyl-4-yloxy)propyl]-3-(2-cyclopentyl-2-hydroxy-2-phenylacetoxy)-1-methylpyrrolidinium trifluoroacetate;
3-(2-Cyclopentyl-2-hydroxy-2-phenylacetoxy)-1-[3-(2,4-difluorophenoxy)propyl]-1-methylpyrrolidinium trifluoroacetate;
3-(2-Cyclopentyl-2-hydroxy-2-phenylacetoxy)-1-ethyl-1-[3-(4-methoxyphenoxy)propyl]-pyrrolidinium trifluoroacetate;
3-(2-Cyclopentyl-2-hydroxy-2-phenylacetoxy)-1-methyl-1-[3-(5,6,7,8-tetrahydronaphthalen-2-yloxy)propyl]pyrrolidinium trifluoroacetate;
3-(2-Cyclopentyl-2-hydroxy-2-phenylacetoxy)-1-methyl-1-[3-(1-methyl-1H-imidazol-2-ylsulphanyl)propyl]pyrrolidinium trifluoroacetate;
3-(2-Hydroxy-2,2-dithien-2-ylacetoxy)-1-[3-(3-hydroxyphenoxy)propyl]-1-methylpyrrolidinium formate;
1-[3-(4-Fluorophenoxy)propyl]-3-(2-hydroxy-2,2-dithien-2-ylacetoxy)-1-methylpyrrolidinium chloride;
3-(2-Cyclohexyl-2-fur-2-yl-2-hydroxyacetoxy)-1-ethyl-1-(3-phenylsulfanylpropyl)pyrrolidinium bromide.

18. A compound according to claim 1 chosen from:
(3R)-3-(2-Hydroxy-2,2-dithien-2-ylacetoxy)-1-methyl-1-(2-phenoxyethyl)pyrrolidinium bromide;
(3S)-3-(2-Hydroxy-2,2-dithien-2-ylacetoxy)-1-methyl-1-(2-phenoxyethyl)pyrrolidinium bromide;
(3R)-3-(2-Hydroxy-2,2-dithien-2-ylacetoxy)-1-methyl-1-(3-phenoxypropyl)pyrrolidinium bromide;
(3S)-3-(2-Hydroxy-2,2-dithien-2-ylacetoxy)-1-methyl-1-(3-phenoxypropyl)pyrrolidinium bromide;
(3R)-3-[(2R)-2-Cyclohexyl-2-fur-2-yl-2-hydroxyacetoxy]-1-ethyl-1-(3-phenylsulphanylpropyl)pyrrolidinium trifluoroacetate;

(3S)-3-[(2R)-2-Cyclohexyl-2-fur-2-yl-2-hydroxyacetoxy]-1-ethyl-1-(3-phenylsulphanylpropyl)pyrrolidinium trifluoroacetate;

(3R)-3-[(2R)-2-Cyclopentyl-2-hydroxy-2-phenylacetoxy]-1-methyl-1-(3-phenoxypropyl)pyrrolidinium bromide;

(3S)-3-[(2R)-2-Cyclopentyl-2-hydroxy-2-phenylacetoxy]-1-methyl-1-(3-phenoxypropyl)pyrrolidinium bromide;

(3R)-3-[(2S)-2-Cyclopentyl-2-hydroxy-2-phenylacetoxy]-1-methyl-1-(3-phenoxypropyl)pyrrolidinium bromide;

(3S)-3-[(2S)-2-Cyclopentyl-2-hydroxy-2-phenylacetoxy]-1-methyl-1-(3-phenoxypropyl)pyrrolidinium bromide;

(3S)-3-(2-Hydroxy-2,2-dithien-2-ylacetoxy)-1-[3-(3-hydroxyphenoxy)propyl]-1-methylpyrrolidinium formate;

(3R)-1-[3-(3-Cyanophenoxy)propyl]-3-(2-cyclohexyl-2-fur-2-yl-2-hydroxyacetoxy)-1-methylpyrrolidinium formate;

(3R)-3-(2-Cyclohexyl-2-fur-2-yl-2-hydroxyacetoxy)-1-methyl-1-[3-(naphthalen-1-yloxy)propyl]pyrrolidinium formate;

(3R)-1-[3-(Benzothiazol-2-yloxy)propyl]-3-(2-cyclohexyl-2-fur-2-yl-2-hydroxyacetoxy)-1-methylpyrrolidinium chloride;

(3R)-1-[3-(Biphenyl-4-yloxy)propyl]-3-[(2R)-2-cyclopentyl-2-hydroxy-2-phenylacetoxy]-1-methylpyrrolidinium chloride;

(3R)-3-[(2R)-2-Cyclopentyl-2-hydroxy-2-phenylacetoxy]-1-methyl-1-[3-(5,6,7,8-tetrahydronaphthalen-2-yloxy)propyl]pyrrolidinium bromide;

(3R)-3-[(2R)-2-Cyclopentyl-2-hydroxy-2-phenylacetoxy]-1-methyl-1-[3-(1-methyl-1H-imidazol-2-ylsulfanyl)propyl]pyrrolidinium chloride;

(3R)-1-[3-(2-Chlorophenoxy)propyl]-3-[(2R)-2-cyclopentyl-2-hydroxy-2-phenylacetoxy]-1-methylpyrrolidinium chloride;

3-[(2R)-2-Cyclopentyl-2-hydroxy-2-phenylacetoxy]-1-ethyl-1-[3-(4-methoxyphenoxy)propyl]pyrrolidinium bromide; and (3R)-1-(2-Benzyloxyethyl)-3-(2-cyclohexyl-2-fur-2-yl-2-hydroxyacetoxy)-1-methylpyrrolidinium bromide.

19. A compound according to claim 1 chosen from:

(1*,3R)-3-(2-Hydroxy-2,2-dithien-2-ylacetoxy)-1-methyl-1-(2-phenoxyethyl)pyrrolidinium bromide (diastereomer 1);

(1*,3R)-3-(2-Hydroxy-2,2-dithien-2-ylacetoxy)-1-methyl-1-(2-phenoxyethyl)pyrrolidinium bromide (diastereomer 2);

(1*,3S)-3-(2-Hydroxy-2,2-dithien-2-ylacetoxy)-1-methyl-1-(2-phenoxyethyl)pyrrolidinium bromide (diastereomer 1);

(1*,3S)-3-(2-Hydroxy-2,2-dithien-2-ylacetoxy)-1-methyl-1-(2-phenoxyethyl)pyrrolidinium bromide (diastereomer 2).

(1*,3R)-3-(2-Hydroxy-2,2-dithien-2-ylacetoxy)-1-methyl-1-(3-phenoxypropyl)pyrrolidinium bromide (diastereomer 1);

(1*,3R)-3-(2-Hydroxy-2,2-dithien-2-ylacetoxy)-1-methyl-1-(3-phenoxypropyl)pyrrolidinium bromide (diastereomer 2);

(1*,3S)-3-[(2R)-2-Cyclopentyl-2-hydroxy-2-phenylacetoxy]-1-methyl-1-(3-phenoxypropyl)pyrrolidinium bromide (diastereomer 1);

(1*,3S)-3-[(2R)-2-Cyclopentyl-2-hydroxy-2-phenylacetoxy]-1-methyl-1-(3-phenoxypropyl)pyrrolidinium bromide (diastereomer 2);

(1*,3S)-1-[3-(4-Fluorophenoxy)propyl]-3-(2-hydroxy-2,2-dithien-2-ylacetoxy)-1-methylpyrrolidinium chloride (diastereomer 1);

(1*,3S)-1-[3-(4-Fluorophenoxy)propyl]-3-(2-hydroxy-2,2-dithien-2-ylacetoxy)-1-methylpyrrolidinium chloride (diastereomer 2);

(1*,3R)-3-[(2R)-2-Cyclopentyl-2-hydroxy-2-phenylacetoxy]-2-methyl-1-(3-phenoxypropyl)pyrrolidinium bromide (disatereomer 1);

(1*,3R)-3-[(2R)-2-Cyclopentyl-2-hydroxy-2-phenylacetoxy]-1-methyl-1-(3-phenoxypropyl)pyrrolidinium bromide (diastereomer 2);

(1*,3R)-1-[3-(Biphenyl-4-yloxy)propyl]-3-[(2R)-2-cyclopentyl-2-hydroxy-2-phenylacetoxy]-1-methylpyrrolidinium chloride (diastereomer 1);

(1*,3R)-1-[3-(Biphenyl-4-yloxy)propyl]-3-[(2R)-2-cyclopentyl-2-hydroxy-2-phenylacetoxy]-1-methylpyrrolidinium chloride (diastereomer 2);

(1*,3R)-3-[(2R)-2-Cyclopentyl-2-hydroxy-2-phenylacetoxy]-1-methyl-1-[3(5,6,7,8-tetrahydronaphthalen-1-yloxy)propyl]pyrrolidinium bromide (diastereomer 1); and (1*,3R)-3-[(2R)-2-Cyclopentyl-2-hydroxy-2-phenylacetoxy]-1-methyl-1-[3(5,6,7,8-tetrahydronaphthalen-1-yloxy)propyl]pyrrolidinium bromide (diastereomer 2).

20. A compound chosen from:

2-Hydroxy-2,2-dithien-2-ylacetic acid (3R)-1-(2-phenoxyethyl)pyrrolidin-3-yl ester; and 2-Hydroxy-2,2-dithien-2-ylacetic acid (3R)-1-(3-phenoxypropyl)pyrrolidin-3-yl ester.

21. A compound (3R)-1-(3-phenoxypropyl)pyrrolidin-3-ol.

22. A pharmaceutical composition comprising a compound as claimed in claim 1 and at least one pharmaceutically acceptable carrier or diluent.

23. A composition according to claim 22 comprising (i) a compound as claimed in claim 1; and (ii) at least one compound chosen from steroid.

* * * * *

UNITED STATES PATENT AND TRADEMARK OFFICE
CERTIFICATE OF CORRECTION

PATENT NO. : 7,192,978 B2
APPLICATION NO. : 10/510680
DATED : March 20, 2007
INVENTOR(S) : Maria Prat Quinones et al.

It is certified that error appears in the above-identified patent and that said Letters Patent is hereby corrected as shown below:

Claim 19, col. 46, lines 35 and 39,
"etoxy]-1-methyl-1-[3(5,6,7,8-tetrahydronaphthalen-1-" should read
--etoxy]-1-methyl-1-[3(5,6,7,8-tetrahydronaphthalen-2--.

Signed and Sealed this

Fifth Day of June, 2007

JON W. DUDAS
*Director of the United States Patent and Trademark Office*